United States Patent [19]

Schirlin et al.

[11] Patent Number: 5,717,093
[45] Date of Patent: Feb. 10, 1998

[54] DIFLUORO STATONE ANALOGS

[75] Inventors: Daniel Schirlin, Lampertheim; Viviane Van Dorsselaer; Céline Tarnus, both of Strasbourg, all of France

[73] Assignee: Merrell Pharmaceuticals Inc., Cincinnati, Ohio

[21] Appl. No.: 578,698

[22] PCT Filed: Jun. 7, 1994

[86] PCT No.: PCT/US94/06376

§ 371 Date: Dec. 18, 1995

§ 102(e) Date: Dec. 18, 1995

[87] PCT Pub. No.: WO95/01958

PCT Pub. Date: Jan. 19, 1995

[30] Foreign Application Priority Data

Jul. 8, 1993 [EP] European Pat. Off. ............. 93401785

[51] Int. Cl.⁶ ...................................... A61K 31/27
[52] U.S. Cl. ........................ 544/130; 544/131; 546/182; 546/348; 560/27
[58] Field of Search ...................... 544/130, 131; 546/187, 348; 560/27

[56] References Cited

U.S. PATENT DOCUMENTS 5,066,643  11/1991  Abeles et al. .

FOREIGN PATENT DOCUMENTS

| 0275101 | 7/1988 | European Pat. Off. . |
|---|---|---|
| 0352000 | 1/1990 | European Pat. Off. . |
| 0386611 | 9/1992 | European Pat. Off. . |
| 2171103 | 8/1986 | United Kingdom . |
| 2196958 | 5/1988 | United Kingdom . |
| 2203740 | 10/1988 | United Kingdom . |
| 2212158 | 7/1989 | United Kingdom . |
| 8606379 | 11/1986 | WIPO . |
| 9000399 | 1/1990 | WIPO . |
| 9212123 | 7/1992 | WIPO ................... C07C 271/22 |
| 9217176 | 10/1992 | WIPO . |
| 9319059 | 9/1993 | WIPO . |
| 9323373 | 11/1993 | WIPO . |
| 9323379 | 11/1993 | WIPO . |
| 9602499 | 2/1996 | WIPO . |

OTHER PUBLICATIONS

Journal of Medicinal Chemistry vol. 29, No. 10, pp. 2080–2087 (1986) S. Thaisrivongs et al. "Design and synthesis of potent and specific renin inhibitors containing difluorostatine, difluorostatone, and related analogues".

Journal of Medicinal Chemistry vol. 35, No. 1, pp. 2–14 (1992)—A.M. Doherty et al. "Design and synthesis of potent, selective, and orally actie fluorine–containing renin inhibitors".

*Primary Examiner*—Robert Gerstl
*Attorney, Agent, or Firm*—Nelson L. Lentz; Carolyn D. Moon

[57] ABSTRACT

This invention relates to novel difluoro statone analogs, to the processes and intermediates useful for their preparation and to their use as anti-viral agents.

12 Claims, No Drawings

DIFLUORO STATONE ANALOGS

This application is A 371 of PCT/US94/06376 filed Jun. 7, 1994.

This invention relates to novel statone analogs, to the processes and intermediates useful for their preparation and to their use as anti-viral agents.

BACKGROUND OF THE PRESENT INVENTION

Retroviruses are a class of viruses which transport their genetic material as ribonucleic acid rather than as deoxyribonucleic acid. Retroviruses are associated with a wide variety of diseases in man, one of which is AIDS. Although there have been disclosures of other anti-viral agents useful in the treatment of AIDS, for example see patent applications EP 0 218 688, EP 0 352 000 and PCT/US 91/09741, the compounds of the present invention have not been previously disclosed. PCT/US 91/09741 is hereby incorporated by reference.

DESCRIPTION OF THE PRESENT INVENTION

More specifically this invention relates to novel difluoro statone analogs of Formula 1

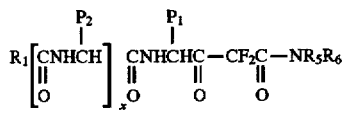

and the stereoisomers, hydrates, isosteres and the pharmaceutically acceptable salts thereof wherein $P_1$ is Q or B, wherein
B is

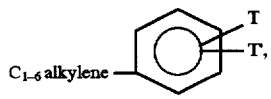

wherein

T is $[(O)_b$—W—R] and T' is $[(O)_{b'}$—W'—R'] or H, wherein each of W and W' are independently $C_{1-6}$ alkylene or nothing and R and R' are each independently —CH$_2$CHO, hydroxy $C_{1-6}$ alkyl, $C_{1-6}$ alkoxy $C_{1-6}$ alkyl, $C_{1-6}$ alkyl, Q,

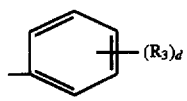

or $R_7$;

provided that W is $C_{2-6}$ alkylene when W is directly attached to a nitrogen atom in R, provided that W' is $C_{2-6}$ alkylene when W' is directly attached to a nitrogen atom in R', provided that W or W' are each independently $C_{1-6}$ alkylene when R or R' are each independently an aryl, and provided that B is other than p-hydroxybenzyl or p-alkoxybenzyl;

Q is

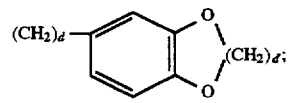

$P_2$ is $C_{1-6}$ alkyl, cyclopentyl, hydroxy $C_{1-6}$ alkyl, phenyl, benzyl or 3-tetrahydrofuryl;

$R_1$ is benzyloxy, $C_{1-6}$ alkoxy, $C_{1-6}$ alkyl, phenyl, benzyl, phenethyl, fluorenylmethylenoxy, 2-isoquinolinyl, PDL,

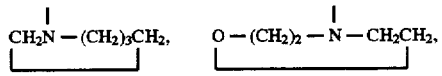

NHSO$_2$R$_4$, N(R$_4$)(benzyl), or N(R$_4$)(PDL),
wherein
PDL is —(CH$_2$)$_a$-2-,3-, or 4-pyridyl, or p-substituted benzyloxy, wherein the substitution is a nitro, OH, amino, $C_{1-6}$ alkoxy, hydroxy $C_{1-6}$ alkylene, or halogeno;

$R_3$ is $C_{1-6}$ alkenyl, $C_{1-6}$ alkoxy, hydroxy $C_{1-6}$ alkyl, $C_{1-6}$ alkyl, or OH;

$R_4$ is H, $C_{1-6}$ alkyl, phenyl or benzyl;

$R_5$ is $C_{7-15}$ alkyl, $C_{7-15}$ alkoxy, CH([(CH$_2$)$_d$—O—CH$_2$]$_x$—R$_8$)$_2$, branched-chain

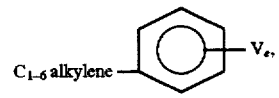

or CH(Y)(Z) wherein
Y is $C_{1-15}$alkyl, hydroxy $C_{1-15}$ alkyl or

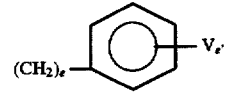

and

Z is (CH$_2$)$_d$—O—CHO, $C_{1-6}$ alkylene-O—(CH$_2$)$_d$—(O—CH$_2$—CH$_2$)$_e$—O—$C_{1-6}$ alkyl,

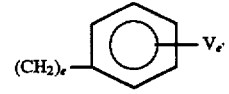

or (CH$_2$)$_d$—O(CH$_2$)$_d$R$_7$ provided that d'=2 when R$_7$ is piperazinyl, substituted piperazinyl, piperidyl or morpholinyl,
wherein V is OR$_4$ or hydroxy $C_{1-6}$ alkyl;

$R_6$ is H or $C_{1-3}$ alkyl;

$R_7$ is piperazinyl, substituted piperazinyl, piperidyl, morpholinyl, pyridyl, pyrazinyl, pyrimidinyl or phenyl, wherein substituted piperazinyl is piperazinyl substituted on one nitrogen atom thereof with CHO, C(O)NHR$_4$, $C_{1-4}$ alkyl or CO$_2$R$_4$;

$R_8$ is pyrimydyl, pyridyl, pyrazinyl or phenyl;
a is zero, 1, 2 or 3;
b and b' are each independently zero or 1;
d and d' are each independently 1 or 2;

e and e' are each independently zero, 1 or 2; and
x is zero or one.

Isosteres of the compounds of Formula I include those wherein (a) the α-amino acid residues of the $P_1$ and $P_2$ substituents are in their unnatural configuration (when there is a natural configuration) or (b) when the normal peptidic carbamoyl linkage is modified, such as for example, to form
—CH₂NH— (reduced),

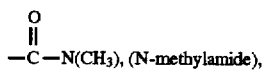
—C—N(CH₃), (N-methylamide),

—COCH₂— (keto), —CH(OH)CH₂— (hydroxy), —CH(NH₂)CH₂— (amino), —CH₂CH₂— (hydrocarbon). Preferably a compound of the invention should not be in an isosteric form. Unless otherwise stated the α-amino acids are preferably in their L-configuration.

A compound of the invention may be in free form, e.g., amphoteric form, or in salt, e.g., acid addition or anionic salt, form. A compound in free form may be converted into a salt form in an art-known manner and vice-versa.

The pharmaceutically acceptable salts of the peptide of Formula I (in the form of water, or oil-soluble or dispersible products) include the conventional non-toxic salts or the quaternary ammonium salts of these peptides, which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkalimetal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The hydrates of the compounds of Formula I are hydrated compounds having the partial structure

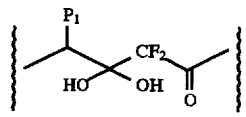

and in their end-use application are generally the active forms.

In general, as used herein, the term "alkyl" includes the straight, branched-chain and cyclized manifestations thereof unless otherwise indicated, particularly such moieties as methyl, ethyl, isopropyl, n-butyl, t-butyl, —CH₂-t-butyl, cyclopropyl, n-propyl, pentyl, cyclopentyl, n-hexyl, cyclo-hexyl and cyclohexylmethyl. The term "aralkyl", when used, includes those aryl moieties attached to an alkylene bridging moiety, preferably methyl or ethyl.

"Aryl" includes both carbocyclic and hetereocyclic moieties of which phenyl, pyridyl, pyrimidinyl, pyazinyl, indolyl, indazolyl, furyl and thienyl are of primary interest; these moieties being inclusive of their position isomers such as, for example, 2-, 3-, or 4-pyridyl, 2- or 3-furyl and thienyl, 1-, 2-, or 3-indolyl or the 1- and 3-indazolyl, as well as the dihydro and tetrahydro analogs of the furyl and thienyl moieties. Also included within the term "aryl" are such fused carbocyclic moieties as pentalenyl, indenyl, naphthalenyl, azulenyl, heptalenyl, acenaphthylenyl, fluorenyl, phenalenyl, phenanthrenyl, anthracenyl, acephenanthrylenyl, aceanthrylenyl, triphenylenyl, pyrenyl, chrysenyl and naphthacenyl. Also included within the term "aryl" are such other heterocyclic radicals as 2- or 3-benzo[b]thienyl, 2- or 3-naphtho[2,3-b]thienyl, 2- or 3-thianthrenyl, 2H-pyran-3-(or 4- or 5-)yl, 1-isobenzofuranyl, 2H-chromenyl-3-yl, 2- or 3-phenoxathiinyl, 2- or 3-pyrrolyl, 4- or 3-pyrazolyl, 2-pyrazinyl, 2-pyrimidinyl, 3-pyridazinyl, 2-indolizinyl, 1-isoindolyl, 4H-quinolizin-2-yl, 3-isoquinolyl, 2-quinolyl, 1-phthalazinyl, 1,8-naphthyridinyl, 2-quinoxalinyl, 2-quinazolinyl, 3-cinnolinyl, 2-pteridinyl, 4aH-carbazol-2-yl, 2-carbazolyl, β-carbolin-3-yl, 3-phenanthridinyl, 2-acridinyl, 2-perimidinyl, 1-phenazinyl, 3-isothiazolyl, 2-phenothiazinyl, 3-isoxazolyl, 2-phenoxazinyl, 3-isochromanyl, 7-chromanyl, 2-pyrrolin-3-yl, 2-imidazolidinyl, 2-imidazolin-4-yl, 2-pyrazolidinyl, 3-pyrazolin-3-yl, 2-piperidyl, 2-piperazinyl, 1-indolinyl, 1-isoindolinyl, 3-morpholinyl, benzo[b]isoquinolinyl and benzo[b]furanyl, including the position isomers thereof except that the heterocyclic moieties cannot be attached directly through their nitrogen one, two or three substituents independently selected from $C_{1-6}$ alkyl, haloalkyl, alkoxy, thioalkoxy, aminoalkylamino, dialkylamino, hydroxy, halo, mercapto, nitro, carboxaldehyde, carboxy, carboalkoxy and carboxamide.

Likewise the term "alkylene" includes straight or branched-chain moieties. Some examples of branched-chain alkylene moieties are ethylethylene, 2-methyltrimethylene, 2,2-dimethyltrimethylene, and so on. For example, $C_3$ alkylene can mean

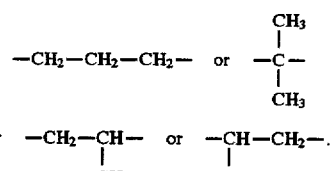

All $(C_{1-15})$ moieties are preferably $(C_{1-6})$ moieties and all $(C_{1-6})$ moieties such as $C_{1-6}$ alkyl, $C_{1-6}$ allenyl, $C_{1-6}$ alkoxy, and hydroxy $C_{1-6}$ alkyl, are more preferably $C_{1-3}$ moieties (containing 1–3 carbon atoms instead of 1–6 carbon atoms).

The fluorenylmethyloxy moiety is that moiety generally called by its abbreviation FMOC, and is the fluorenyl moiety bearing —CH₂O— attached to the 9-position of the fluorenyl moiety. Other terms defined herein are piperazinyl

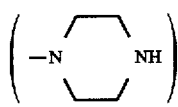

or substituted piperazinyl

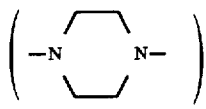

the substitution (★) occurring only at one nitrogen molecule which is not attached to the remainder of the molecule (attachment via a nitrogen atom). The substituents are one of CHO, C(O)NHR$_4$, C$_{1-4}$ alkyl or CO$_2$R$_4$.

Piperidyl and morpholinyl both bind to the rest of the

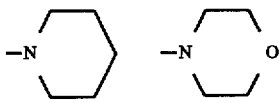

molecule via their respective nitrogen atoms while pyrimidinyl, pyridyl and pyrazinyl bind to the rest

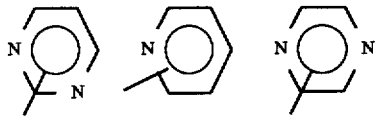

of the molecule anywhere except their respective nitrogen atoms.

More specifically, in the instance wherein P$_2$ is either C$_{1-6}$ alkyl or hydroxy C$_{1-6}$ alkyl, such moieties as —C(CH$_3$)$_3$, —CH(CH$_3$)$_2$, —CH(CH$_3$)(C$_2$H$_5$), —C(OH)(CH$_3$)$_2$ and —CH(OH)CH$_3$ are preferred. The "hydroxy C$_{1-6}$ alkyl" moiety is illustrated in one example by —CH$_2$—OH, the "C$_{1-6}$ alkoxy C$_{1-6}$ alkyl" moiety, is illustrated in one example by —CH$_2$—OCH$_3$, (although in each instance the C$_{1-6}$ alkylene may be straight or branched and the hydroxy radical is not limited to the terminal carbon atom of the alkyl moiety). The

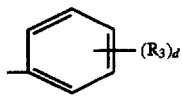

moiety shows a phenyl moiety which may be substituted with one or two of the R$_3$ moieties (said moieties being the same or different).

As it is often quite advantageous to have what is termed an amino protecting group (Pg), the scope of those compounds of Formula I, includes those R$_1$ moieties which, together with their adjacent carbonyl moiety form such groups as acetyl (Ac), succinyl (Suc), benzoyl (Bz), t-butyloxycarbonyl (Boc), benzyloxycarbonyl (CBZ), tosyl (Ts), dansyl (DNS), isovaleryl (Iva), methoxysuccinyl (MeOSuc), 1-adamantanesulphonyl (AdSO$_2$), 1-adamantaneacetyl (AdAc), phenylacetyl, t-butylacetyl (Tba), bis[(1-naphthyl)methyl]acetyl (BNMA) and Rz wherein Rz is an aryl group as previously described suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolo, and acylsulfonamido (i.e., acylaminosulfonyl and sulfonylaminocarbonyl) containing from 1 to 15 carbons, provided that when the acylsulfonamido contains an aryl. The aryl may be further substituted by a member selected from fluoro, chloro, bromo, iodo and nitro.

In those instances wherein there is an Rz moiety, it is preferred that Rz represent acylsulfonamido, particularly those wherein the acylsulfonamido contains an aryl moiety (preferably phenyl) substituted by a halogen. The preferred Rz moieties being 4-[(4-chlorophenyl)sulfonylaminocarbonyl]phenylcarbonyl, 4-[(4-bromophenyl)sulfonylaminocarbonyl]-phenylcarbonyl and 4-[phenylsulfonylamino carbonyl]-phenylcarbonyl (said moieties being abbreviated as 4-Cl-Ø-SAC-Bz, 4-Br-Ø-SAC-Bz and Ø-SAC-Bz, respectively).

Among the classes of amino protecting groups contemplated are: (1) acyl type protecting groups such as formyl, trifluoroacetyl, phthalyl, p-toluenesulfonyl (tosyl), benzenesulfonyl, nitrophenylsulfenyl, tritylsulfenyl, O-nitrophenoxyacetyl, and α-chlorobutyryl; (2) aromatic urethane type protecting groups such as benzyloxycarbonyl and substituted benzyloxycarbonyls such as p-chlorobenzyloxycarbonyl, p-methoxybenzyloxycarbonyl, p-nitrobenzyloxycarbonyl, p-bromobenzyloxycarbonyl, 1-(p-biphenylyl)-1-methylethoxycarbonyl, α,α-dimethyl-3, 5-dimethoxybenzyloxycarbonyl, and benzhydryloxycarbonyl; (3) aliphatic urethane protecting groups such as tert-butyloxycarbonyl (Boc), diisopropylmethoxycarbonyl, isopropyloxycarbonyl, ethoxycarbonyl, and allyloxycarbonyl; (4) cycloalkyl urethane type protecting groups such as cyclopentyloxycarbonyl, adamantyloxycarbonyl, and cyclohexyloxycarbonyl; (5) thio urethane type protecting groups such as phenylthiocarbonyl; (6) alkyl type protecting groups such as triphenylmethyl (trityl) and benzyl (Bzl); (7) trialkylsilane protecting groups such as trimethylsilane if compatible. The preferred α-amino protecting groups are tert-butyloxycarbonyl (Boc) or benzyloxycarbonyl (CBZ). The use of Boc as an α-amino protecting group for amino acids is described by Bodansky et al. in "The Practice of Peptide Synthesis", Springer-Verlag, Berlin (1984), p. 20.

In general the compounds of this invention may be prepared using standard chemical reactions analogously known in the art.

In the instance wherein it is desired to prepare compounds of the formula

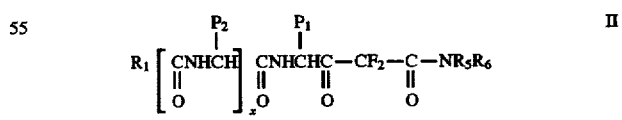

wherein R$_1$, P$_2$, P$_1$, R$_5$ and R$_6$ are as previously defined, the process outlined by the following reaction scheme may advantageously be utilized.

REACTION SCHEME A

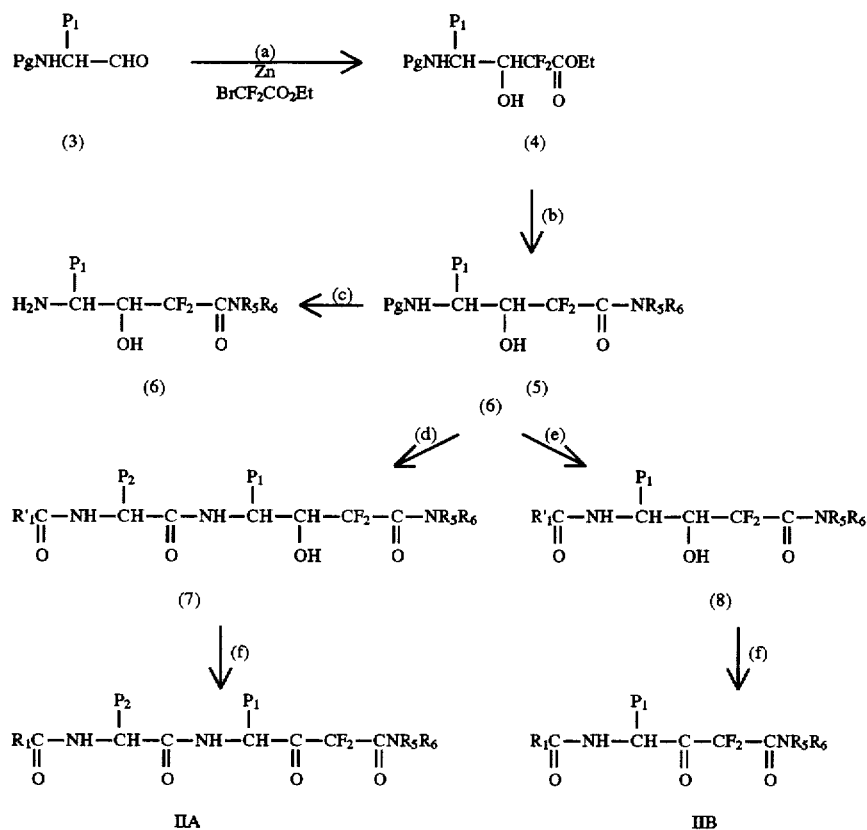

wherein R'₁ represents optional amino protecting groups, as herein above defined, and the $R_1$, $P_1$, $P_2$, $R_5$ and $R_6$ moieties are as previously defined.

In effecting reaction scheme A, the process is initiated by conducting a Reformatsky-type reaction wherein an aldehyde of Formula (3) is subjected to a condensation reaction with an ester of bromodifluoroacetic acid, preferably the ethyl ester in the presence of zinc and in an anhydrous aprotic solvent, e.g., tetrahydrofuran, ether, dimethoxyethane and the like under a nitrogen or argon inert atmosphere. The reaction is gently heated to about 60° C. for about 1–12 hours or ultrasonicated to produce compounds (4). Step (b) to obtain compounds (5) may be effected directly or undirectly. In one instance, the esters of Formula (4) are de-esterified using a strong base (LiOH, KOH, NaOH and the like) in the presence of water using a partially water miscible solvent (such as tetrahydrofuran, dimethoxyethane, dioxane) at about room temperature. The so-obtained de-esterified compound is then aminated with the appropriate $R_5R_6$-substituted amine using a peptide-like coupling procedure—i.e., using a mixed anhydride method using DCC and hydroxybenzotriazole at room temperature in solvents such as $CH_2Cl_2$, tetrahydrofuran or dimethylformamide. Alternatively the esters (4) may be directly subjected to a reaction with the appropriate $R_5R_6$-substituted amine without or with a solvent (tetrahydrofuran) at about 80° C. Following the preparation of compounds (5), the protecting groups Pg may readily be removed by standard procedures, e.g., hydrogenation or acid base hydrolysis. Compounds (6) are subjected to a peptide coupling procedure with an appropriately protected acid of the formulae $R_1CONH(P_2)COOH$ or $R_1CO_2H$, using the herein-described procedures (or by any other coupling procedure currently available) to produce compounds (7) and (8), respectively. At this point, if desired, the amide formed with $R_1$ may be optionally deprotected, or if desired, the amide may be replaced with another amide within the scope of $R_1$. The alcohols of (7) and (8) are then oxidized to the corresponding ketones and, if desired, the compounds may be converted to their pharmaceutically acceptable salts.

The oxidation may be effected via the well-known Swern oxidation procedure, or with 1,1,1-triacetoxy-2,1-benzoxiodol (Dess-Martin reagent). The coupling procedures are effected according to standard procedures well known in the art.

"Swern oxidation" is well known in the art [see Synthesis, (1981), 165]. For example, it may be effected by reacting about 2 to 20 equivalents of dimethylsulfoxide (DMSO) with about 1 to 10 equivalents of trifluoromethylacetic anhydride [$(CF_3CO)_2O$] or oxalyl chloride [$(COCl)_2$], said reactants being dissolved in an inert solvent, e.g., methylene chloride ($CH_2Cl_2$), said reaction being under an inert atmosphere (e.g., nitrogen or equivalently functioning gas) under anhydrous conditions at temperatures of about −70° C. to −30° C. to form an in situ sulfonium adduct to which is added about 1 equivalent of the appropriate alcohols, i.e., compounds (7) and (8). Preferably, the alcohols are dissolved in an inert solvent, e.g., $CH_2Cl_2$, tetrahydrofuran, or minimum amounts of DMSO, and the reaction mixture is allowed to warm to about −50° C. or −20° C. (for about 20–60 minutes) and then the reaction is completed by adding about 3 to 30 equivalents of a tertiary amine, e.g., triethylamine, diisopropylethylamine, N-methyl morpholine, etc.

Another alternative process for converting the alcohols to the desired ketones is an oxidation reaction which is called the "Dess Martin oxidation" reaction and employs periodane (i.e., 1,1,1-triacetoxy-2,1-benzoxiodol), [see Dess Martin, *J. Org. Chem.*, 48, 4155, (1983)]. This oxidation is effected by contacting about 1 equivalent of the alcohols with 1 to 5 equivalents of periodane (preferably 1.5 equivalents), said reagent being in suspension in an inert solvent (e.g., methylene chloride) under an inert atmosphere (preferably nitrogen) under anhydrous conditions at 0° C. to 50° C. (preferably room temperature) and allowing the reactants to interact for about 1 to 48 hours. Optional deprotection of the amine protecting groups may be effected as desired after the ketones have been isolated.

In general, the modified Jones oxidation procedure may conveniently be effected by reacting the alcohols with pyridinium dichromate by contacting the reactants together in a water-trapping molecular sieve powder, e.g., a grounded 3 Ångström molecular sieve), wherein said contact is in the presence of glacial acetic acid at about 0° C. to 50° C., preferably at room temperature followed by isolation and then optionally removing amine protecting groups.

Alternatively, 1 to 5 equivalents of a chromic anhydride-pyridine complex (i.e., a Sarett reagent prepared in situ) [see Fieser and Fieser "Reagents for Organic Synthesis" Vol. 1, pp. 145 and Sarett, et al., J.A.C.S. 25, 422, (1953)] said complex being prepared in situ in an inert solvent (e.g., $C_2Cl_2$) in an inert atmosphere under anhydrous conditions at 0° C. to 50° C. to which complex is added 1 equivalent of the alcohols allowing the reactants to interact for about 1 to 15 hours, followed by isolation and optionally removing amine protecting groups.

In certain instances, it may be preferably to introduce the appropriate $P_1$ group after the $R_5R_6$ group is attached. In those instances, $P_1$ may comprise a protecting group until after step (a). For example, $P_1$ at compound (3) may be 4-(benzyloxy)benzyl which can be hydrogenated to the phenol, preferably by catalytic hydrogenation after steps (a) or (b). Introduction of the remainder of the appropriate $P_1$ moiety can be accomplished after steps (b), (d) or (e) by alkylation under basic conditions such as cesium or potassium carbonate with X—$C_{1-6}$ alkylene R wherein X is an appropriate leaving group such as halogeno or triflate, in the presence of a solvent such as dioxane, tetrahydro-furan or dimethylformamide.

For the preparation of the necessary aldehydes of (3), and the preparation of the acids which are to be coupled with the amines of Formula (6), alternative alkylation procedures are utilized depending upon whether the $P_1$ and/or the $P_2$ moieties are or are not residues of natural amino acids. The preparation of these intermediates wherein the $P_1$ or $P_2$ moieties are residues of natural amino acids (or minor modifications thereof, e.g., $P_1$ or $P_2$ being a methyl ether of tyrosine), the compounds are either known or are prepared by processes and techniques well known in the art.

To prepare the intermediates of the formula

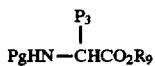  (9)

wherein Pg is an amino protecting group, $P_3$ is either a $P'_1$ or $P'_2$ moiety with $P'_1$ and $P'_2$ being as defined for $P_1$ and $P_2$ respectively, except that they are other than residues of naturally occuring amino acids, and the $R_9$ moiety is an alkyl radical, preferably methyl when $P_3$ is $P'_1$, and ethyl when $P_3$ is $P'_2$, alternative methods are available.

To prepare the intermediates of formulae

the following reaction scheme may be utilized

REACTION SCHEME B

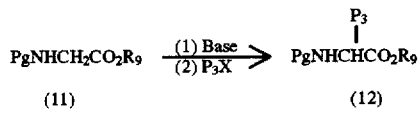

wherein $P_3$ is as previously defined and X is a leaving group, preferably halo or triflate, $R_9$ is methyl when $P_3$ is $P'_1$, and ethyl when $P_3$ is $P'_2$.

In essence, the preparation of compounds (12) utilizes the Krapcho method [Tetrahedron Letters, 26, 2205 (1976)] for alkylation wherein compounds (11) are treated with a base, e.g., LDA, (lithium diisopropylamide), followed by reaction with the desired $P_3X$ in the presence of TMEDA (i.e. tetramethylethylenediamine) in a solvent (tetrahydrofuran) with or without HMPA (i.e. hepamethylphosphonamide) according to the standard Krapcho conditions. Following alkylation the compounds are then subjected to a reduction using diisobutyl aluminum hydride (Dibal) in a mixture of solvents, e.g., ether, toluene, hexane, tetrahydrofuran at about −78° C. for about 1 hour. Following the preparation of the aldehydes of Formula (10B), the compounds are subjected to the processes of Reaction Scheme A.

Alternatively, the compounds of (12) may be prepared by a Malonate/Curtius type sequence of reactions, [see Yamada, et al., J. Amer. Chem. Soc., (1972) 94, 6203] as illustrated by the following reaction scheme

REACTION SCHEME C

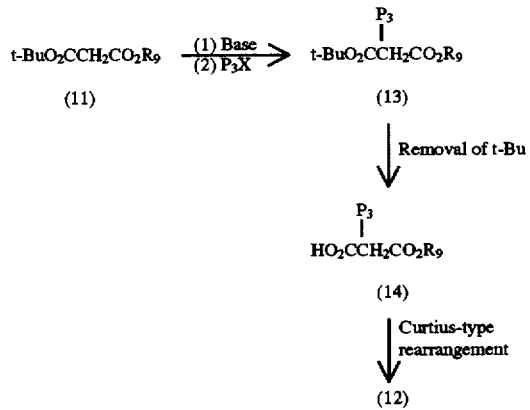

wherein t-Bu is t-butyl, although other selectively removal acid protecting groups may be utilized, and $P_3X$ is as previously defined. This reaction involves the alkylation of the malonate ester (11) followed by selective removal of the t-butyl protecting group to produce compounds (14). These compounds are then transformed to (12) using the Curtius type rearrangement which entails their conversion to the protected amine via the intermediately formed azides, isocyanates, amines which are then protected with standard amino protecting groups, preferentially being protected in situ.

In the instance wherein P₃ represents a P'₁ moiety, the ester is transformed to the desired aldehydes of Formula (3) using standard Dibal reduction techniques, particularly in this situation (wherein P₁ is not a residue of a natural amino acid). Alternatively, (as is preferred when P₁ is a residue of a natural amino acid) the ester is de-esterified to its corresponding acid, converted to its corresponding hydroxamate and the hydroxamate upon treatment with lithium aluminum hydride is converted to its aldehyde. In the instance wherein P₃ represents a P'₂ moiety, the ethyl ester of compounds (12) are removed and the resulting compounds are ready for coupling as outlined in Reaction Scheme A.

Having generically described the methods for the preparation of the compounds of this invention, the following specific examples illustrate the chemistry and techniques by which the synthesis may be effected.

EXAMPLE 1

O-(3-Pyridylmethyl)-(D)-valinol

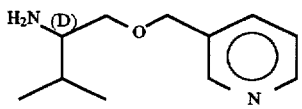

STEP A
N-TRITYL-(D)-VALINOL

A solution of (D)-Valinol (4.95 g, 48.06 mmol), triethylamine (7.4 ml, 52.87 mmol) and trityl chloride (14.74 g, 52.87 mmol) in dry dichloromethane (75 ml) was stirred for 17 hours at room temperature. The organic solution was washed twice with water (2×75 ml) and dried over sodium sulfate. After filtration and concentration in vacuo, the resulting oil (22.4 g) was purified by flash chromatography (silica gel, ethyl acetate/petroleum ether: 15/85) to give the title compound in 81% yield (13.5 g, hard oil).

Rf.: 0.45 (ethyl acetate/petroleum ether: 15/85).

STEP B
N-TRITYL-O-(3-PYRIDYLMETHYL)-(D)-VALINOL

Under nitrogen, to a suspension of sodium hydride (1.3 g, 30 mmol, 55% dispersion in oil, previously washed twice with pentane) in dry dimethylformamide (3 ml) was added under stirring a solution of N-trityl-(D)-valinol (3.45 g, 10 mmol) in dimethylformamide (23 ml). To the reaction mixture kept for 30 minutes at room temperature and then cooled down to 0° C., was added as a solid tetrabutylammonium iodide (0.37 g, 1 mmol). After addition in portions over 5 minutes of solid 3-picolyl chloride hydrochloride (1.81 g, 11 mmol), the cooling bath was removed and the mixture was stirred for 17 hours at room temperature. The reaction mixture, previously cooled in an ice bath, was hydrolyzed with water (100 ml) and extracted twice with ethyl acetate (2×100 ml). The organic phases were washed until neutral with water (2×50 ml) and the combined organic layers were dried over sodium sulfate. Filtration and concentration in vacuo yielded a yellow oil (4.8 g) which was purified by flash chromatography (silica gel, dichloromethane/ethyl acetate: 9/1, Rf.: 0.42). The title compound was obtained as an oil (3.4 g, 78% yield).

STEP C
O-(3-PYRIDYLMETHYL)-(D)-VALINOL

A solution of N-trityl-O-(3-pyridyl)methyl-(D)-valinol (3.63 g, 8.3 mmol) in formic acid (30 ml) was kept for 5.5 hours at room temperature. After removal of the formic acid in vacuo, the residue was dissolved in water (100 ml) and extracted twice with ethyl acetate (100 ml, 50 ml) in order to remove trityl alcohol. The aqueous phase was basified with a saturated solution of sodium carbonate (50 ml) and 4N sodium hydroxyde (3 ml) and extracted with ethyl acetate (4×50 ml). After washing with brine until neutral (2×50 ml), the combined organic layers were dried over sodium sulfate. After usual work-up, the resulting amine was used without further purification (1.32 g, 82% yield).

Rf.: 0.12 (silica gel, dichloromethane/methanol: 8/2).

EXAMPLE 2

O-(2-Pyridylmethyl)-(D)-valinol

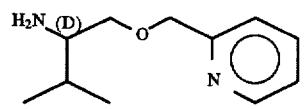

STEP A
N-TRITYL-O-(2-PYRIDYLMETHYL)-(D)-VALINOL

The title compound was prepared in 81% yield from the compound given in Example 1, Step A using the alkylation procedure described in Example 1 Step B, with 2-picolyl chloride, hydrochloride instead of the 3-derivative.

Rf.: 5.1 (silica gel, dichloromethane/ethyl acetate: 9/1).

STEP B
O-(2-PYRIDYLMETHYL)-(D)-VALINOL

The title amine was obtained in 80% yield from the compound of Example 2, Step A using the formic acid deprotection described in Example 1, Step C.

EXAMPLE 3

O-[2-(2-Methoxyethoxy)-1-ethyl]-(D)-valinol

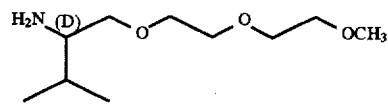

STEP A
N-TRITYL-O-[2-(2-METHOXYETHOXY)-1-ETHYL]-(D)-VALINOL

The title derivative was prepared in 86% yield from the compound of Example 1, Step A using 2-(2-methoxyethoxy)ethyl-1-bromide as reagent in the alkylation procedure described in Example 1, Step B.

Rf.: 0.74 (silica gel, acetone/petroleum ether: 2/8).

STEP B
O-[2-(2-METHOXYETHOXY)-1-ETHYL]-(D)-VALINOL

A solution of N-Trityl-O-[2-(2-methoxyethoxy)-1-ethyl]-(D)-valinol (1.0 g, 2.28 mmol) in dry ether saturated with HCl gaz (20 ml) was kept for 2.5 hours at room temperature. After concentration in vacuo, the resulting solid (1.16 g) was purified by flash chromatography (silica gel, dichloromethane first to elute trityl alcohol and then dichloromethane/diethylamine: 95/5, Rf.: 0.20) to give the title free amine as a colorless oil (0.46 g, quantitative).

EXAMPLE 4

O-Benzyl-(D)-valinol

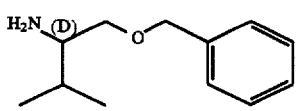

STEP A
N-TERT-BUTOXYCARBONYL-(D)-VALINOL

A solution of (D)-valinol (5.1 g, 49.4 mmol) and di-tert-butyldicarbonate (10.9 g, 50 mmol) in methanol (60 ml) was stirred for 17 hours at room temperature. After concentration in vacuo, the residue was purified by flash chromatography (silica gel, ethyl acetate/petroleum ether: 3/7, Rf.: 0.37) to give the title compound in quantitative yield (10.07 g, colorless oil).

MS: MH$^+$=204.

STEP B
N-TERT-BUTOXYCARBONYL-O-BENZYL-(D)-VALINOL

To a solution of N-tert-butoxycarbonyl-(D)-valinol (10 g, 49.3 mmol) and benzylbromide (5.86 ml, 49.3 mmol) in anhydrous DMF (50 ml) was added at −5° C. and under nitrogen, potassium-tert-butoxide (11.06 g, 98.6 mmol) as a solid, portionwise, and in such a way that the internal temperature does not exceed +5° C. The reaction mixture was stirred for 2 hours at 0° C., diluted with ethyl acetate (2×300 ml), extracted with a 1N solution of potassium hydrogenosulfate (50 ml) and water (250 ml) and washed twice with water (2×200 ml). After drying of the organic phase on sodium sulfate, filtration and concentration in vacuo, the resulting oil was purified by flash chromatography (silica gel, ethyl acetate/petroleum ether: 1/9, Rf.: 0.42) to give the title compound as a colorless oil (9.95 g, 69% yield).

MS: MH$^+$=294.

STEP C
O-BENZYL-(D)-VALINOL

A solution of N-tert-Butoxycarbonyl-D-benzyl-(D)-valinol (9.95 g, 34 mmol) in formic acid (50 ml) was stirred for 4 hours at room temperature. After removal of the formic acid in vacuo, the sticky residue was dissolved in water (100 ml), neutralized with a saturated solution of sodium bicarbonate (100 ml) and the organic material extracted twice with ethyl acetate (2×200 ml). The organic phases were washed until neutral with water (2×100 ml) and the combined organic layers were dried on sodium sulfate. Filtration and evaporation of the solvent in vacuo afforded the title amine as a slightly yellowish oil (5.20 g, 79%).

MS: MH$^+$=194.

EXAMPLE 5
O-2-Methoxyethoxymethyl-(D)-valinol

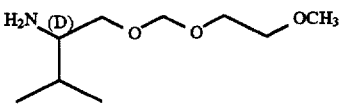

STEP A
N-TERT-BUTOXYCARBONYL-O-(2-METHOXYETHOXYMETHYL)-(D)-VALINOL

To a solution of N-tert-butoxycarbonyl-(D)-valinol (2.03 g, 10 mmol) in anhydrous dimethylformamide (20 ml) cooled under nitrogen at −10° C., was added 1-methoxyethoxymethyl chloride (1.37 ml, 12 mmol) and then in two portions potassium tert-butoxide (1.35 g, 12 mmol, rinced with 10 ml of dimethylformamide). The cooling bath being removed, the reaction mixture was stirred for 3.5 hours at room temperature. After hydrolysis with water (~5 ml), the major part of the solvent was removed with a high vacuum pomp. The residue was taken up in slightly acidic water (potassium hydrogenosulfate), extracted twice with ethyl acetate (2×100 ml) and the organic phases washed with water until neutral (2×50 ml). Usual work-up afforded an oil (2.8 g) which was purified by flash chromatography (silica gel, petroleum ether/ethyl acetate: 7/3; Rf.: 0.43) to give the title ether in 37% yield.

MS: MH$^+$=292, MNH$_4^+$=309.

STEP B
O-(2-METHOXYETHOXYMETHYL)-(D)-VALINOL

The title amine was obtained in 77% yield from the compound of Example 5, Step A using the procedure described in Example 4, Step C, the washings being performed with brine to avoid the loss of this amine in the aqueous phase.

EXAMPLE 6
4-tert-Butoxycarbonylamino-2,2-difluoro-3-hydroxy-5(4-benzyloxy)phenyl pentanoic acid, ethyl ester

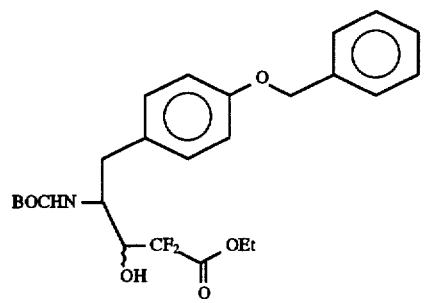

STEP A
N-TERT-BUTOXYCARBONYL-L-O-BENZYLTYROSINE-N,O-DIMETHYLHYDROXAMATE

A mixture of N-tert-butoxycarbonyl-L-O-benzyltyrosine (37.1 g, 100 mmol), dicyclohexylcarbodiimide (20.6 g, 100 mmol) and N-hydroxybenzotriazole, hydrate (15.3 g, 100 mmol) in anhydrous dichloromethane (350 ml) was stirred at 0° C. for 10 minutes. To that mixture were added, at 0° C., N,O-dimethylhydroxylamine hydrochloride (9.75 g, 100 mmol) and N-methylmorphiline (10.1 g, 100 mmol). The temperature was allowed to raise to room temperature while the stirring was continued for 15 hours. The white precipitate was filtered off, rinsed with dichloromethane. The filtrate was evaporated to dryness. The crude mixture was purified by flash chromatography (silica gel, ethyl acetate/cyclohexane: 2/8). 34.3 g of the expected hydroxamate were isolated as a white solid (83% yield).

Rf: 0.36 (ethyl acetate/cyclohexane: 1/1).

STEP B
N-TERT-BUTOXYCARBONYL-L-O-BENZYLTYROSINAL

To a solution of N-tert-butoxycarbonyl-L-O-benzyltyrosine, N,O-dimethylhydroxamate (18.2 g, 44 mmol) in a 4:1 mixture of anhydrous diethylether and dimethoxyethane (300 ml) was added at 0° C., portionwise, lithium aluminium hydride (1.82 g, 48 mmol). Stirring was continued for 1.5 hours at 0° C. Hydrolysis was done by dropwise addition of a 1M solution of potassium hydrogeno sulfate (55 ml). The aqueous phase was decanted and reextracted with ethyl acetate (2×200 ml). The combined organic layers were washed with 3N hydrochloric acid (250 ml) and brine (200 ml). The organic phase was dried over anhydrous magnesium sulfate. Filtration and removal of the solvent in vacuo yielded the expected aldehyde as a white solid. Recrystallization from ethyl acetate/pentane afforded 13 g of crystalline N-tert-butoxycarbonyl-L-O-benzyltyrosinal.

Rf: 0.51 (silica gel, ethyl acetate/cyclohexane: 1/1).
STEP C
4-TERT-BUTOXYCARBONYLAMINO-2,2-DIFLUORO-3-HYDROXY-5-(4-BENZYLOXY) PHENYLPENTANOIC ACID, ETHYL ESTER To a suspension of zinc (1.95 g, 30 matg) in anhydrous tetrahydrofuran (5 ml) was added, under nitrogen, a mixture of ethyl bromodifluoroacetate (6.09 g, 30 mmol) and N-tert-butoxycarbonyl-L-O-benzyltyrosinal (3.55 g, 10 mmol) in anhydrous tetrahydrofuran (25 ml). After addition of 2 ml of that solution, the suspension was heated at reflux with stirring. Gentle reflux was maintained by slow addition (dropwise) of the rest of the solution of aldehyde and bromoester. The mixture was stirred for 4 additional hours at room temperature after completion of the addition. Hydrolysis was performed by addition of 1M sulfuric acid (20 ml) and the mixture was extracted with ethyl acetate (3×50 ml). The combined organic layers were washed with brine and dried over anhydrous magnesium sulfate. Filtration and removal of the solvent in vacuo afforded an oil that was purified by flash chromatography (silica gel, gradient of ethyl acetate/cyclohexane: 1/9 to 3/7). 1.8 g of the title compound were isolated (38% yield).

Rf: 0.55 and 0.5 (ethyl acetate/cyclohexane: 1/1).

Analysis calculated for $C_{25}H_{31}NO_6F_2$: C: 62.62 H: 6.52 N: 2.92 Found: C: 62.81 H: 6.67 N: 3.05

EXAMPLE 7

N-[4-(N-Benzyloxycarbonyl-1-valyl)amino-2,2-difluoro-1,3-dioxo-5-(4-benzyloxy)phenyl-pentyl]-O-[(3-pyridyl)methyl]-D-valinol The title compound was prepared in 91% yield from the carbamate of Example 7, Step A following the deprotection procedure described in Example 4, Step C using sodium carbonate instead of sodium bicarbonate.

MS: $MH^+$=528.

STEP C
N-[4-(N-BENZYLOXYCARBONYL-L-VALYL)AMINO-2,2-DIFLUORO-3-HYDROXY-1-OXO-5-(4-BENZYLOXY)PHENYL-PENTYL]-O-[(3-PYRIDYL)METHYL]-D-VALINOL

To a solution of N-benzyloxycarbonyl-L-valine (0.101 g, 0.4 mmol) in anhydrous dimethylformamide (2 ml) were added under nitrogen N-hydroxybenzotriazole, hydrate (0.115 g, 0.4 mmol) and 1-ethyl-3(3-dimethylaminopropyl) carbodiimide, hydrochloride (0.085 g, 0.44 mmol) with the help of 1 ml of dimethylformamide. To the reaction mixture stirred for 0.5 hour at room temperature was added the amine of Example 7, Step B (0.211 g, 0.4 mmol) with 1 ml of dimethylformamide. The stirring was continued for 15 hours and the reaction mixture was diluted with ethyl acetate (80 ml) and washed twice with water (2×80 ml), the aqueous phases being extracted a second time with ethyl acetate (80 ml). The combined organic layers were dried over sodium sulfate. After filtration and concentration in vacuo, the solid residue (0.360 g) was purified by flash chromatography (silica gel, dichloromethane/ethanol: 95/5.

Rf: 0.23) to give the title compound in 85% yield (0.260 g).

MS: $MH^+$=761.

Analysis calculated for $C_{42}H_{50}N_4O_7F_2$: C: 66.38 H: 6.62 N: 7.36 Found: C: 66.68 H: 6.68 N: 7.40

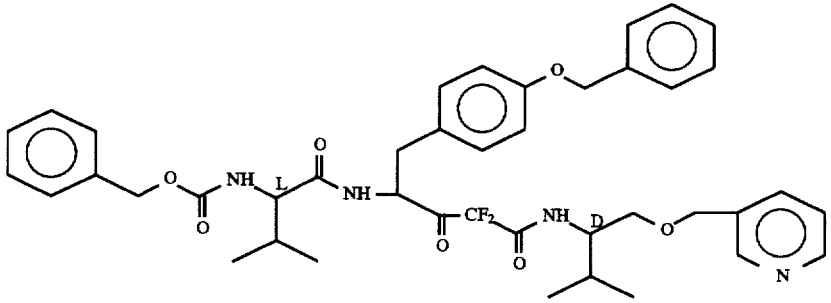

STEP A
N-[4-TERT-BUTOXYCARBONYLAMINO-2,2-DIFLUORO-3-HYDROXY-1-OXO-5-(4-BENZYLOXY)PHENYL-PENTYL]-O-[(3-PYRIDYL)METHYL]-D-VALINOL

A solution of 1.14 g (2.38 mmol) of the ester of Example 6, Step C and 1.32 g (6.8 mmol) of the amine of Example 1, Step C in dry tetrahydrofuran (1.5 ml) was heated for 2 days under reflux. After cooling, the reaction mixture was diluted with ethyl acetate (5 ml), pentane (10 ml) and the precipitate thus obtained was filtered off and rinsed with pentane. The residue (1.25 g) was recrystallized from a mixture of dichloromethane/drops of methanol/pentane and the title compound was obtained as a white solid (0.8 g, 54% yield).

Rf: 0.5 (silica gel, ethyl acetate).
MS: $MH^+$=628.

STEP B
N-[4-AMINO-2,2-DIFLUORO-3-HYDROXY-1-OXO-5-(4-BENZYLOXY)PHENYL-PENTYL]-O-[(3-PYRIDYL)METHYL]-D-VALINOL

STEP D
N-[4-(N-BENZYLOXYCARBONYL-L-VALYL)AMINO-2,2-DIFLUORO-1,3-DIOXO-5-(4-BENZYLOXY)PHENYL-PENTYL]-O-[(3-PYRIDYL)METHYL]-D-VALINOL

To a solution of oxalyl chloride (0.23 ml, 2.63 mmol) in anhydrous dichloromethane (1 ml) at −60° C. was added under nitrogen, freshly distilled dimethylsulfoxide (0.42 ml, 5.26 mmol) in 2 ml of dichloromethane. After 10 minutes of stirring at −60° C., the temperature was allowed to rise to −20° C. Immediately was added dropwise to that mixture a solution of the alcohol of Example 7, Step C (0.2 g, 0.263 mmol) in dichloromethane (7 ml) and dimethylsulfoxide (1 ml). After stirring for 3.5 hours at −20° C., the reaction mixture was cooled down to −78° C., hydrolyzed with diisopropyl ethyl amine (1.24 ml, 8.94 mmol) and kept for 5 more minutes at −78° C. The cooling bath was removed and the mixture was allowed to return to room temperature. After dilution with dichloromethane (25 ml), the mixture was washed twice with water (2×25 ml), the aqueous layers being extracted again with dichloromethane (25 ml). The combined organic phases were dried on sodium sulfate. After filtration and concentration in vacuo, the residue (0.240 g) was purified by flash chromatography (silica gel, dichloromethane/ethyl acetate: 30/70 followed by neutral alumina act. III, tetrahydrofuran/dichloromethane/water: 10/20/0.1, in order to remove residual starting material) to give the title ketone in 37% yield (0.075 g).

Rf: 0.23 (silica gel, dichloromethane/ethyl acetate: 30/70).

MS: MH$^+$=759.

Analysis calculated for $C_{42}H_{48}N_4O_7F_2$, 0.5 $H_2O$: C: 65.70 H: 6.43 N: 7.30 Found: C: 65.49 H: 6.34 N: 7.14

EXAMPLE 8

4-(N-Benzyloxycarbonyl-L-valyl)amino-2,2-difluoro-3-oxo-5-(4-benzyloxy)phenyl-N(1-isopropyl-2-methylpropane)pentanamide

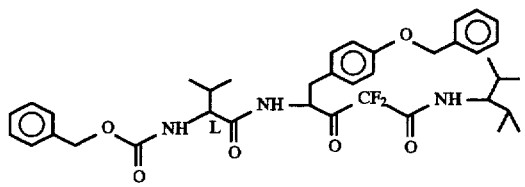

STEP A
4-TERT-BUTOXYCARBONYLAMINO-2,2-DIFLUORO-3-HYDROXY-5-(4- BENZYLOXY)PHENYL-N(1-ISOPROPYL-2-METHYL-PROPANE)PENTANAMIDE

A solution of the ester of Example 6, Step C (0.50 g, 1.04 mmol) in 0.77 ml of 3-amino-2,4-dimethyl pentane (5.2 mmol) was heated at 75° C. for 90 hours. After dilution with ethyl acetate (15 ml), extraction with 1N potassium hydrogeno sulfate (15 ml) and washing with water (2×15 ml)—the aqueous phases being extracted again with ethyl acetate (15 ml)—the combined organic layers were dried over sodium sulfate. Filtration and concentration of the solvent afforded a residue (0.54 g) which was purified by flash chromatography (silica gel, petroleum ether/ethyl acetate: 75/25, Rf: 0.34) to give the title compound in 42% yield (0.24 g).

MS: MH$^+$=549.

STEP B
4-AMINO-2,2-DIFLUORO-3-HYDROXY-5-(4-BENZYLOXY)PHENYL-N(1-ISOPROPYL-2-METHYL-PROPANE)PENTANAMIDE

The title amine was obtained in 92% yield from the compound of Example 8, Step A, using the deprotection method described in Example 7, Step B.

MS: MH$^+$=449.

STEP C
4-(N-BENZYLOXYCARBONYL-L-VALYL)AMINO-2,2-DIFLUORO-3-HYDROXY-5-(4-BENZYLOXY) PHENYL-N(1-ISOPROPYL-2-METHYLPROPANE) PENTANAMIDE

To a stirred solution of N-benzyloxycarbonyl-L-valyl anhydride (0.181 g, 0.37 mmol) and the amine described in Example 8, Step, B (0.140 g, 0.31 mmol) in anhydrous dimethylformamide (3 ml) was added under nitrogen 0.041 ml of N-methylmorpholine (0.37 mmol). The reaction mixture was kept overnight at room temperature, diluted with water (15 ml) and extracted with ethyl acetate (2×15 ml), the organic layers being washed a second time with water (15 ml) and then dried over sodium sulfate. After filtration, removal of the solvent in vacuo and purification of the residue (8.200 g) by flash chromatography (silica gel, dichloromethane/ethyl acetate: 85/15, Rf: 0.16) the title compound was obtained as a white solid (0.080 g, 38% yield).

MS: MH$^+$=682.

STEP D
4-(N-BENZYLOXYCARBONYL-L-VALYL)AMINO-2,2-DIFLUORO-3-OXO-5-(4-BENZYLOXY)PHENYL-N(1-ISOPROPYL-2-METHYL-PROPANE)PENTANAMIDE

The title compound was obtained in 51% yield from the alcohol of Example 8, Step C using the Swern oxidation depicted in Example 7, Step D.

MS: MH$^+$=680, MNH$_4^+$=697.

Analysis calculated for $C_{39}H_{41}N_3O_6F_2$: C: 64.14 H: 6.97 N: 6.18 Found: C: 64.53 H: 6.57 N: 5.75

EXAMPLE 9

4-[N-(3-Pyridylpropionyl)-L-valyl]amino-2,2-difluoro-3-oxo-5-(4-benzyloxy)phenyl-N(1-isopropyl-2-methylpropane)pentanamide

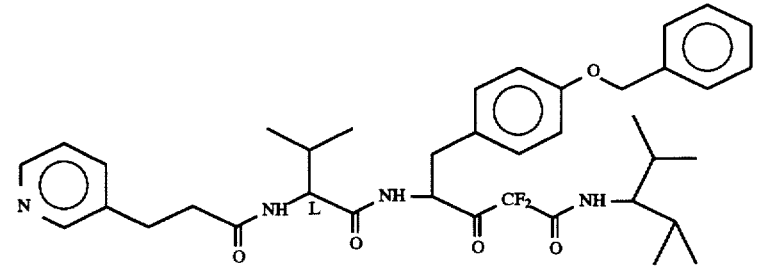

STEP A
4-(N-TERT-BUTOXYCARBONYL-L-VALYL)AMINO-2, 2-DIFLUORO-3-HYDROXY-5-(4-BENZYLOXY) PHENYL-N(1-ISOPROPYL-2-METHYLPROPANE) PENTANAMIDE

The title compound was prepared in 76% yield from the amine of Example 8, Step B and N-tert-butoxycarbonyl-L-valine using the coupling procedure given in Example 7, Step C with dichloromethane as solvent instead of dimethylformamide.

Rf: 0.17 (silica gel, dichloromethane/ethyl acetate: 90/10).

MS: MH$^+$=648.

STEP B
4-(L-VALYL)AMINO-2,2-DIFLUORO-3-HYDROXY-5-(4-BENZYLOXY)PHENYL-N(1-ISOPROPYL-2-METHYL-PROPANE)PENTANAMIDE

The title amine was prepared in quantitative yield from the compound described in Example 9, Step A, using the procedure given in Example 7, Step B.

MS: MH+=548.

STEP C
4-[N-(3-PYRIDYLPROPIONYL)-L-VALYL]AMINO-2,2-DIFLUORO-3-HYDROXY-5-(4-BENZYLOXY)

PHENYL-N(1-ISOPROPYL-2-METHYLPROPANE) PENTANAMIDE

The title compound was obtained in 84% yield from the amine of Example 9, Step B and 3-pyridylpropionic acid using the coupling method described in Example 7, Step C.

Rf: 0.16 (silica gel, ethyl acetate)

MS: MH+=681.

Analysis calculated for $C_{38}H_{50}N_4O_5F_2$: C: 67.04 H: 7.40 N: 8.23 Found: C: 67.34 H: 7.60 N: 7.74

STEP D
4-[N-(3-PYRIDYLPROPIONYL)-L-VALYL]AMINO-2,2-DIFLUORO-3-OXO-5-(4-BENZYLOXY)PHENYL-N(1-ISOPROPYL-2-METHYL-PROPANE)PENTANAMIDE

The title compound was prepared in 57% yield from the alcohol of Example 9, Step C using the Swern oxidation procedure described in Example 7, Step D.

Rf: 0.2 (silica gel, ethyl acetate);

Analysis calculated for $C_{38}H_{48}N_4O_5F_2$, 0.75 $H_2O$: C: 65.92 H: 7.21 N: 8.09 Found: C: 65.93 H: 7.21 N: 7.92

EXAMPLE 10

N-[4-(N-Benzyloxycarbonyl-L-valyl)amino-2,2-difluoro-1,3-dioxo-5-(4-benzyloxy)phenyl-pentyl]-di(O-benzyl) serinol hydrogeno sulfate (15 ml) and washed twice with water (2×15 ml), the aqueous phases being extracted again with 15 ml of ethyl acetate. After drying of the organic layers on sodium sulfate, filtration and concentration in vacuo, the residue (0.52 g) was purified by flash chromatography (silica gel, petroleum ether/ethyl acetate: 70/30, Rf: 0.35) to give the title derivative in 52% yield (0.33 g).

STEP E
N-[4-AMINO-2,2-DIFLUORO-3-HYDROXY-1-OXO-5-(4-BENZYLOXY)PHENYL-PENTYL]-DI(O-BENZYL) SERINOL

The title amine was obtained in 92% yield from the compound of Example 10, Step D using the deprotection procedure given in Example 7, Step B.

STEP F
N-[4-(N-BENZYLOXYCARBONYL-L-VALYL]AMINO-2,2-DIFLUORO-3-HYDROXY-1-OXO-5-(4-BENZYLOXY)PHENYL-PENTYL]-DI(O-BENZYL) SERINOL

The title compound was obtained in 47% yield from the amine given in Example 10, Step E and N-benzyloxycarbonyl-L-valyl anhydride following the coupling procedure described in Example 8, Step c and using dichloromethane as solvent.

RF: 0.30 (silica gel, dichloromethane/ethyl acetate: 90/10).

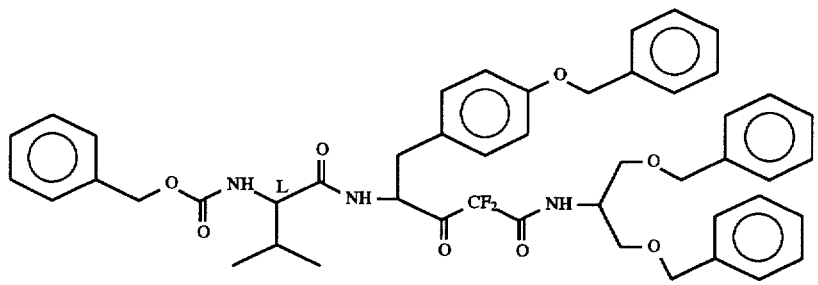

STEP A
N-TERT-BUTOXYCARBONYL SERINOL

The title derivative was prepared as a white solid in 94% yield from commercially available serinol using the protection procedure described in Example 4, Step A.

Rf: 0.33 (silica gel, ethyl acetate).

STEP B
N-TERT-BUTOXYCARBONYL-DI(O-BENZYL) SERINOL

The title compound was prepared in 49% yield from N-tert-butoxycarbonyl serinol using the procedure given in Example 4, Step B, but using tetrahydrofuran as solvent, 2.4 equivalents of benzyl bromide and 2.2 equivalents of potassium-tert-butoxide.

RF: 0.17 (silica gel, petroleum ether/ethyl acetate: 90/10).

STEP C
DI(O-BENZYL)SERINOL

The title amine was prepared in 80% yield from the compound depicted in Example 10, Step B, following the deprotection method described in Example 7, Step B.

STEP D
N-[4-TERT-BUTOXYCARBONYLAMINO-2,2-DIFLUORO-3-HYDROXY-1-OXO-5-(4-BENZYLOXY) PHENYL-PENTYL]-DI(O-BENZYL)SERINOL

A solution of the ester of Example 6, Step C (0.256 g, 0.534 mmol) and di(O-benzyl)serinol (0.43 g, 1.6 mmol) in dry tetrahydrofuran (2 ml) was heated under reflux during 40 hours. After removal of the solvent, the residue was taken up in ethyl acetate (15 ml), extracted with 1N potassium

MS: MH+=838, MNH$_4$+=855.

STEP G
N-[4-(N-BENZYLOXYCARBONYL-L-VALYL)AMINO-2,2-DIFLUORO-1,3-DIOXO-5-(4-BENZYLOXY) PHENYL-PENTYL]-DI(O-BENZYL)SERINOL

The title derivative was obtained in 26% yield from the alcohol given in Example 10, Step F, following the Swern oxidation described in Example 7, Step D.

RF: 0.11 (silica gel, petroleum ether/ethyl acetate: 70/30).

MS: MH+=836.

Analysis calculated for $C_{48}H_{51}N_3O_8F_2$, 0.5 $H_2O$: C: 68.23 H: 6.20 N: 4.97 Found: C: 68.02 H: 6.16 N: 4.81

EXAMPLE 11

4-(N-Benzyloxycarbonyl-L-valyl)amino-2,2-difluoro-3-oxo-5-(4-benzyloxy)phenyl-N(α-L-methyl)benzyl pentanamide

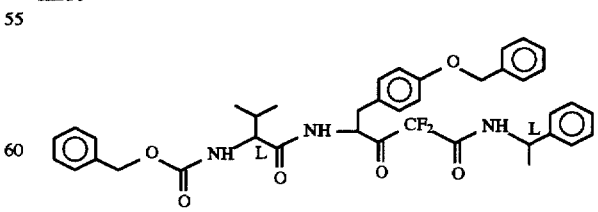

STEP A
4-TERT-BUTOXYCARBONYLAMINO-2,2-DIFLUORO-3-HYDROXY-5-(4-BENZYLOXY)PHENYL-N(α-L-METHYL)BENZYL PENTANAMIDE

The title compound was prepared in 75% yield from the ester of Example 6, Step C and α-L-methyl benzylamine following the procedure depicted in Example 10, Step D.

Rf: 0.06 (silica gel, petroleum ether/ethyl acetate: 80/20).

STEP B
4-AMINO-2,2-DIFLUORO-3-HYDROXY-5-(4-BENZYLOXY)PHENYL-N(α-L-METHYL)BENZYL PENTANAMIDE

The title amine was obtained in 92% yield from the derivative described in Example 11, Step A, using the formic acid deprotection given in Example 7, Step B.

STEP C
4-(N-BENZYLOXYCARBONYL-L-VALYL)AMINO-2,2-DIFLUORO-3-OXO-5-(4-BENZYLOXY)PHENYL-N(α-L-METHYL)BENZYL PENTANAMIDE

The title compound was obtained in 87% yield from the amine of Example 11, Step B and N-benzyloxycarbonyl-L-valyl anhydride using the procedure described in Example 8, Step C and with dichloromethane as solvent.

STEP D
4-(N-BENZYLOXYCARBONYL-L-VALYL)AMINO-2,2-DIFLUORO-3-OXO-5-(4-BENZYLOXY)PHENYL-N(α-L-METHYL)BENZYL PENTANAMIDE

The title derivative was obtained in low yield from the alcohol of Example 11, Step C using the oxidation procedure described in Example 7, Step D (recovery of more than 50% of starting alcohol despite of 2 successive Swern oxidations).

Rf: 0.14 (silica gel, petroleum/ether/ethyl acetate: 70/30).

Analysis calculated for $C_{39}H_{41}N_3O_6F_2$, 0.5 $H_2O$: C: 67.42 H: 6.09 N: 6.05 Found: C: 67.22 H: 5.91 N: 5.74

EXAMPLE 12

N-[4-(N-Benzyloxycarbonyl-L-valyl)amino-2,2-difluoro-1,3-dioxo-5-(4-benzyloxy)phenyl-pentyl]-O-(2-methoxyethoxymethyl)-D-valinol method given in Example 7, Step B, the reaction temperature being kept at 5° C. instead of room temperature.

STEP C
N-[4-(N-BENZYLOXYCARBONYL-L-VALYL)AMINO-2,2-DIFLUORO-3-HYDROXY-1-OXO-5-(4-BENZYLOXY)PHENYL-PENTYL]-O-(2-METHOXYETHOXYMETHYL)-D-VALINOL

The title derivative was prepared in 59% yield from the amine of Example 12, Step B and N-benzyloxycarbonyl-L-valyl anhydride following the procedure described in Example 8, Step C and with dichloromethane as solvent.

Rf: 0.25 (silica gel, dichloromethane/ethyl acetate: 80/20).

MS: $MH^+$=758, $MNH_4^+$=775.

STEP D
N-[4-(N-BENZYLOXYCARBONYL-L-VALYL)AMINO-2,2-DIFLUORO-1,3-DIOXO-5-(4-BENZYLOXY)PHENYL-PENTYL]-O-(2-METHOXYETHOXYMETHYL)-D-VALINOL

The title compound was obtained in 73% yield from the alcohol of Example 12, Step C using the Swern oxidation depicted in Example 7, Step D.

Rf: 0.26 (silica gel, dichloromethane/ethyl acetate: 70/30).

MS: $MH^+$=770.

Analysis calculated for $C_{40}H_{51}N_3O_9F_2$: C: 63.56 H: 6.80 N: 5.56 Found: C: 63.55 H: 6.78 N: 5.49

EXAMPLE 13

N-[4-(N-Benzyloxycarbonyl-L-valyl)amino-2,2-difluoro-1,3-dioxo-5-(4-benzyloxy)phenyl-pentyl]-O-formyl-D-valinol

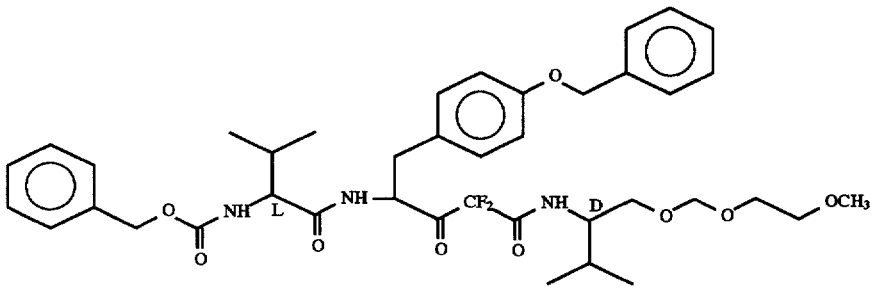

STEP A
N-[4-TERT-BUTOXYCARBONYLAMINO-2,2-DIFLUORO-3-HYDROXY-1-OXO-5-(4-BENZYLOXY)PHENYL-PENTYL]-O-(2-METHOXYETHOXYMETHYL)-D-VALINOL

The title compound was prepared in 56% yield from the ester of Example 6, Step C and the amine of Example 5, Step B using the substitution procedure described in Example 10, Step D.

Rf: 0.35 (silica gel, petroleum ether/ethyl acetate: 55/45).

STEP B
N-[4-AMINO-2,2-DIFLUORO-3-HYDROXY-1-OXO-5-(4-BENZYLOXY)PHENYL-PENTYL]-O-(2-METHOXYETHOXYMETHYL)-D-VALINOL

The title amine was obtained in quantitative yield from the compound of Example 12, Step A using the deprotection

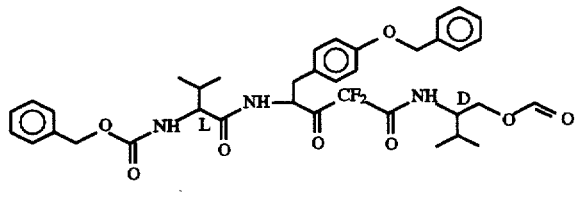

A solution of the compound given in Example 12, Step D (0.050 g, 0.066 mmol) in formic acid (5 ml) was stirred for 5 hours at room temperature. After concentration in vacuo, the residue (0.043 g) was purified by a micro flash chromatography (silica gel, dichloromethane/ethyl acetate: 70/30, Rf: 0.49) to give the title compound in 44% yield.

MS: $MH^+$=696.

EXAMPLE 14

N-[4-(N-Benzyloxycarbonyl-L-valyl)amino-2,2-difluoro-1,3-dioxo-5-(4-benzyloxy)phenyl-pentyl]-O-[2-(2-methoxyethoxy)-1-ethyl]-D-valinol

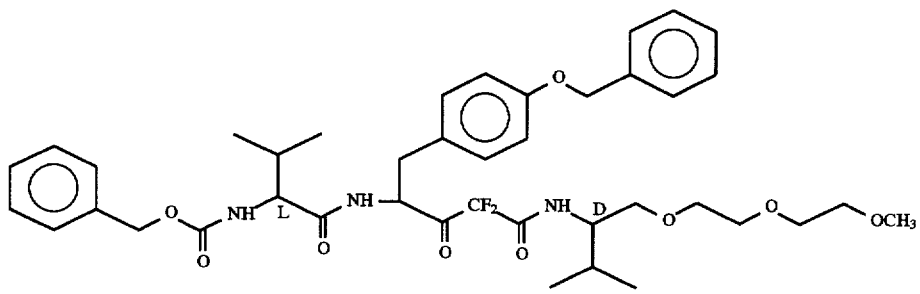

STEP A
N-[4-(TERT-BUTOXYCARBONYLAMINO-2,2-DIFLUORO-3-HYDROXY-1-OXO-5-(4-BENZYLOXY) PHENYL-PENTYL]-O-[2-(2-METHOXYETHOXY)-1-ETHYL]-D-VALINOL

The title compound was prepared in 51% yield from the ester of Example 6, Step C and the amine of Example 3, Step B using the procedure depicted in Example 10, Step D.

Rf: 0.37 (silica gel, petroleum ether/ethyl acetate: 30/70).

STEP B
N-[4-AMINO-2,2-DIFLUORO-3-HYDROXY-1-OXO-5-(4-BENZYLOXY)PHENYL-PENTYL]-O-[2-(2-METHOXYETHOXY)-1-ETHYL]-D-VALINOL

The title amine was obtained in 97% yield from the compound of Example 14, Step A using the deprotection method described in Example 7, Step B.

MS: MH+=539.

STEP C
N-[4-(N-BENZYLOXYCARBONYL-L-VALYL)AMINO-2,2-DIFLUORO-3-HYDROXY-1-OXO-5-(4-BENZYLOXY)PHENYL-PENTYL]-O-[2-(2-METHOXYETHOXY)-1-ETHYL]-D-VALINOL

The title derivative was obtained in 74% yield from the amine of Example 14, Step B and N-benzyloxycarbonyl-L-valyl anhydride using the coupling procedure described in Example 8, Step C and with dichloromethane as solvent.

Rf: 0.19 (major isomer at the 3-hydroxy function) and 0.13 (minor isomer) (silica gel, dichloromethane/ethyl acetate: 60/40).

MS: MH+=772.

STEP D
N-[4-(N-BENZYLOXYCARBONYL-L-VALYL)AMINO-2,2-DIFLUORO-1,3-DIOXO-5-(4-BENZYLOXY) PHENYL-PENTYL -O-[2-(2-METHOXYETHOXY)-1-ETHYL]-D-VALINOL

The title compound was prepared in 74% yield from the alcohol of Example 14, Step C using the oxidation method given in Example 7, Step D.

Rf: 0.13 (silica gel, dichloromethane/ethyl acetate: 70/30).

MS: MH+=770

Analysis calculated for $C_{41}H_{53}N_3O_9F_2$: C: 63.96 H: 6.84 N: 5.46 Found: C: 63.94 H: 6.86 N: 5.38

EXAMPLE 15

4-(N-Benzyloxycarbonyl-L-valyl)amino-2,2-difluoro-3-oxo-5-(4-benzyloxy)phenyl-N-benzydryl pentanamide

STEP A
4-(TERT-BUTOXYCARBONYL)AMINO-2,2-DIFLUORO-3-HYDROXY-5-(4-BENZYLOXY) PHENYL-N-BENZYDRYL PENTANAMIDE

The title compound was obtained in 45% yield from the ester of Example 6, Step C and commercially available benzydrylamine (distilled over potassium hydroxyde) using the procedure described in Example 10, Step D.

Rf: 0.50 (silica gel, cyclohexane/ethyl acetate: 1/1).
MS: MH+=617.

STEP B
4-AMINO-2,2-DIFLUORO-3-HYDROXY-5-[4-BENZYLOXY)PHENYL-N-BENZYDRYL PENTANAMIDE

The title amine was obtained in 82% yield from the derivative of Example 15, Step A following the deprotection method given in Example 7, Step B.

STEP C
4-(N-BENZYLOXYCARBONYL-L-VALYL)AMINO-2,2-DIFLUORO-3-HYDROXY-5-(4-BENZYLOXY) PHENYL-N-BENZYDRYL PENTANAMIDE

The title compound was prepared in 83% yield from the amine of Example 15, Step B and N-benzyloxycarbonyl-L-valyl anhydride following the coupling reaction given in Example 8, Step C using dichloromethane as solvent.

Rf: 0.49 (silica gel, cyclohexane/ethyl acetate: 1/1).
MS: MH+=750.

STEP D
4-(N-BENZYLOXYCARBONYL-L-VALYL AMINO-2,2-DIFLUORO-3-OXO-5-(4-BENZYLOXY)PHENYL-N-BENZYDRYL PENTANAMIDE

The title derivative was obtained from the alcohol of Example 15, Step C using the Swern oxidation depicted in Example 7, Step D.

Rf: 0.47 (silica gel, cyclohexane/ethyl acetate: 1/1).
MS: MH+=748, MNH$_4^+$=765.

Analysis calculated for $C_{37}H_{43}N_3O_8F_2$: C: 63.87 H: 6.23 N: 6.04 Found: C: 64.15 H: 6.35 N: 5.78

Analysis calculated for $C_{44}H_{43}N_3O_6F_2$: C: 70.67 H: 5.79 N: 5.62 Found: C: 69.88 H: 5.89 N: 5.49

EXAMPLE 16

4-(N-Benzyloxycarbonyl-L-valyl)amino-2,2-difluoro-3-oxo-5-(4-benzyloxy)phenyl-N[1,1-di(2-pyridyl)methyl]pentanamide

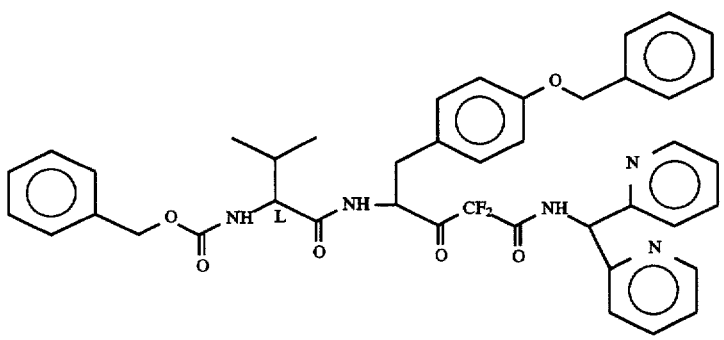

STEP A
N-TERT-BUTOXYCARBONYL-1,1-DI(2-PYRIDYL)METHYL AMINE

To a solution of commercial di(2-pyridyl)ketone (3.68 g, 20 mmol) in anhydrous methanol (60 ml) was added ammonium acetate (15.40 g, 200 mmol) and sodium cyanoborohydride (0.88 g, 14 mmol). After stirring at room temperature for 24 hours, the reaction mixture was hydrolyzed with 37% hydrochloric acid until pH≅2 and the solvent removed in vacuo. The residue was taken off in water (100 ml), extracted twice with diethyl ether (2×60 ml) and the combined organic layers were dried over magnesium sulfate. After filtration and removal of the solvent in vacuo, the residue was taken off in anhydrous dichloromethane (50 ml) and di-tert-butyl dicarbonate (2.80 g, 13 mmol) was added, the reaction mixture being stirred for 16 hours at room temperature. The solvent was removed in vacuo and the residue was purified by flash chromatography (silica gel, cyclohexane/ethyl acetate: 3/7) to give the title compound in 17% yield (0.90 g).

Rf: 0.34 (silica gel, ethyl acetate).

STEP B
1,1-DI(2-PYRIDYL)METHYL AMINE

To a solution of the compound of Example 16, Step A (0.85 g, 3 mmol) in anhydrous diethyl ether (10 ml) was added at 0° C. 40 ml of a saturated solution of hydrogen chloride gas in anhydrous diethyl ether. The reaction mixture was stirred at 0° C. and then the temperature was allowed to rise to room temperature overnight. The solvent was removed in vacuo and the residue was taken off in ethyl acetate (100 ml), washed three times with a saturated solution of sodium carbonate (3×30 ml) and the organic layer dried over magnesium sulfate. Removal of the solvent in vacuo afforded the title compound in 55% yield (0.30 g).

STEP C
4-(TERT-BUTOXYCARBONYL)AMINO-2,2-DIFLUORO-3-HYDROXY-5-(4-BENZYLOXY)PHENYL-N-[1,1-DI(2-PYRIDYL)METHYL]PENTANAMIDE

The title compound was prepared in 43% yield from the ester of Example 6, Step C and the amine of Example 16, Step B following the procedure described in Example 10, Step D.

Rf: 0.40 (silica gel, ethyl acetate)
MS: MH⁺=619.

STEP D
4-AMINO-2,2-DIFLUORO-3-HYDROXY-5-(4-BENZYLOXY)PHENYL-N-[1,1-DI(2-PYRIDYL)METHYL]PENTANAMIDE

The title amine was obtained in 77% yield from the compound of Example 16, Step C using the deprotection method described in Example 7, Step B.

STEP E
4-(N-BENZYLOXYCARBONYL-L-VALYL)AMINO-2,2-DIFLUORO-3-HYDROXY-5-(4-BENZYLOXY)PHENYL-N-[1,1-DI(2-PYRIDYL)METHYL]PENTANAMIDE

The title compound was obtained in 70% yield from the amine of Example 16, Step D and N-benzyloxycarbonyl-L-valyl anhydride using the coupling method depicted in Example 8, Step C using dichloromethane as solvent.

Rf: 0.49 (silica gel, ethyl acetate).
MS: MH⁺=752.

STEP F
4-(N-BENZYLOXYCARBONYL-L-VALYL)AMINO-2,2-DIFLUORO-3-OXO-5-(4-BENZYLOXY)PHENYL-N-[1,1-DI(2-PYRIDYL)METHYL]PENTANAMIDE

The title compound was prepared in 42% yield from the alcohol of Example 16, Step E using the oxidation procedure described in Example 7, Step D.

Rf: 0.39 (silica gel, ethyl acetate).
MS: MH+=750.

Analysis calculated for $C_{42}H_{41}N_5O_6F_2$, 0.5 $H_2O$: C: 66.48 H: 5.58 N: 9.23 Found: C: 66.37 H: 5.55 N: 8.91

EXAMPLE 17

N-[4-(N-Benzyloxycarbonyl-L-valyl)amino-2,2-difluoro-[1,3-dioxo-5-(4-{2-N-morpholyl}ethyloxy)phenyl-pentyl]-O-[(3-pyridyl)methyl]-D-valinol

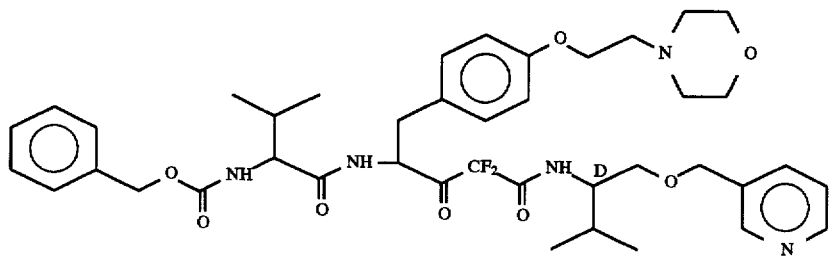

STEP A
4-TERT-BUTOXYCARBONYLAMINO-2,2-DIFLUORO-3-HYDROXY-5-(4-HYDROXY)PHENYL PENTANOIC ACID, ETHYL ESTER

A solution of compound of Example 6, Step C (0.719 g, 1.5 mmol) in ethanol (50 ml) was kept for 7.5 hours under an hydrogen atmosphere in the presence of 10% palladium on charcoal (0.074 g). The hydrogen atmosphere was exchanged by a nitrogen atmosphere, the suspension was filtered off and the solution concentrated in vacuo. The title thus obtained was used as such in the next step (0.500 g, 83% yield).

Rf: 0.51 (silica gel, petroleum ether/ethyl acetate: 1/1).

STEP B
N-[4-TERT-BUTOXYCARBONYLAMINO-2,2-DIFLUORO-3-HYDROXY-1-OXO- 5-(4-HYDROXY)PHENYL-PENTYL]-O-[(3-PYRIDYL)METHYL]-D-VALINOL

The title compound was obtained in 82% yield from the ester of Example 17, Step A and the amine of Example 1, Step C, following the procedure described in Example 10, Step D.

Rf: 0.47 (silica gel, ethyl acetate).

STEP C
N-[4-TERT-BUTOXYCARBONYLAMINO-2,2-DIFLUORO-3-HYDROXY-1-OXO-5-(4-{2-N-MORPHOLYL}ETHYLOXY)PHENYL-PENTYL]-O-[(3-PYRIDYL)METHYL]-D-VALINOL

A solution of the phenolic derivative described in Example 17, Step B (0.081 g, 0.15 mmol) and 4-(2-chloroethyl)morpholine, hydrochloride (0.039 g, 0.21 mmol) in dry dimethylformamide (3 ml) was stirred under nitrogen for 66 hours at room temperature in the presence of cesium carbonate (0.166 g, 0.51 mmol) and potassium iodide (0.0035 mg, 0.021 mmol). The reaction mixture was diluted with ethyl acetate (15 ml) and washed twice with water (2×15 ml), the aqueous phases being extracted again with ethyl acetate (15 ml). After drying of the combined organic layers on sodium sulfate, filtration and concentration in vacuo, the residue (0.117 g) was purified by flash chromatography (silica gel, ethyl acetate/methanol: 90/10, Rf: 0.27) to give the title compound in 51% yield (0.050 g).

MS: $MH^+$=651.

STEP D
N-[4-AMINO-2,2-DIFLUORO-3-HYDROXY-1-OXO-5-(4-{2-N-MORPHOLYL}ETHYLOXY)PHENYL-PENTYL]-O-[(3-PYRIDYL)METHYL]-D-VALINOL

The title amine was prepared in quantitative yield from the derivative of Example 17, Step C following the deprotection procedure described in Example 7, Step B.

MS: $M^+$=551.

STEP E
N-[4-(N-BENZYLOXYCARBONYL-L-VALYL)AMINO-2,2-DIFLUORO-3-HYDROXY-1-OXO-5-(4-{2-N-MORPHOLYL}ETHYLOXY)PHENYL-PENTYL]-O-[(3-PYRIDYL)METHYL]-D-VALINOL

The title compound was obtained in 53% yield from the amine of Example 17, Step D and N-benzyloxycarbonyl-L-valine following the coupling method given in Example 7, Step C.

Rf: 0.17 (silica gel, dichloromethane/ethanol: 95/5).
MS: $MH^+$=784.

Analysis calculated for $C_{41}H_{55}N_5O_8F_2$, $0.25H_2O$: C: 62.46 H: 7.10 N: 8.88 Found: C: 62.41 H: 6.94 N: 8.69

STEP F
N-[4-(N-BENZYLOXYCARBONYL-L-VALYL)AMINO-2,2-DIFLUORO-1,3-DIOXO-5-(4-{2-N-MORPHOLYL}ETHYLOXY)PHENYL-PENTYL]-O-[(3-PYRIDYL)METHYL]-D-VALINOL

The title compound was prepared in 25% yield from the alcohol described in Example 17, Step E using the Swern oxidation depicted in Example 7, Step D.

Rf: 0.06 (silica gel, ethyl acetate/acetone: 8/2).

Analysis calculated for $C_{41}H_{53}N_5O_8F_2$, $H_2O$: C: 61.56 H: 6.93 N: 8.76 Found: C: 61.56 H: 6.80 N: 8.26

Alternative procedure

To a solution of the alcohol of example 17, step E (0.244 g, 0.31 mmol) in freshly distilled dichloromethane (10 ml) was added the Dess-Martin reagent (0.528 g, 1.24 mmol) and tert-butanol (0.06 ml, 0.62 mmol). After stirring for 10 minutes at room temperature, the reaction mixture was quenched with 2-propanol (1 ml) and concentrated in vacuo. The white solid residue was suspended in dichloromethane (4 ml, then 2 ml for rinsing) and the solid part was removed by filtration over a Fluoropore filter. Concentration in vacuo afforded a residue which was purified by flash chromatography (silica gel, dichloromethane/methanol: 98/2 for removing the by-products of the Dess-Martin reagent, then dichloromethane/methanol: 96/4 and finally dichloromethane/methanol: 90/10 to eluate the desired product). The title ketone was obtained as a white solid in 61% yield (0.148 g)

Analysis calculated for $C_{41}H_{53}N_5O_8F_2$,$0.5H_2O$: C: 62.26 H: 6.88 N: 8.86 Found: C: 62.49 H: 6.98 N: 8.97.

EXAMPLE 18

N-[4-(N-Benzyloxycarbonyl-L-valyl)amino-2,2-difluoro-1,3-dioxo-5-(4-{2-N-morpholyl}ethyloxy)phenyl-pentyl]-O-[(2-pyridyl)methyl]-D-valinol

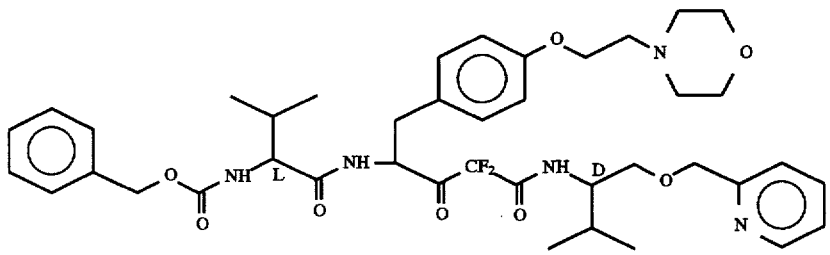

STEP A
N-[4-TERT-BUTOXYCARBONYLAMINO-2,2-DIFLUORO-3-HYDROXY-1-OXO-5-(4-{2-N-MORPHOLYL}ETHYLOXY)PHENYL-PENTYL]-O-[(2-PYRIDYL)METHYL]-D-VALINOL

The title compound was prepared in 67% yield from the ester of Example 17, Step A and the amine of Example 2, Step B using the procedure described in Example 10, Step D.

Rf: 0.29 (silica gel, dichloromethane/ethyl acetate: 3/7).

STEP B
N-[4-AMINO-2,2-DIFLUORO-3-HYDROXY-1-OXO-5-(4-HYDROXY)PHENYL-PENTYL]-O-[(2-PYRIDYL)METHYL]-D-VALINOL

The title amine was obtained in 96% yield from the derivative of Example 18, Step A following the deprotection method given in Example 7, Step B.

MS: MH$^+$=438.

STEP C
N-[4-(N-BENZYLOXYCARBONYL-L-VALYL)AMINO-2,2-DIFLUORO-3-HYDROXY-1-OXO-5-(4-BENZYLOXY)PHENYL-PENTYL]-O-[(2-PYRIDYL)METHYL]-D-VALINOL

The title derivative was obtained in 47% yield from the amine of Example 18, Step B and N-benzyloxycarbonyl-L-valine using the coupling procedure described in Example 7, Step C.

Rf: 0.31 (silica gel, dichloromethane/ethyl acetate: 2/8).
MS: MH+=671.

STEP D
N-[4-N-BENZYLOXYCARBONYL-L-VALYL)AMINO-2,2-DIFLUORO-3-HYDROXY-1-OXO-5-(4-{2-N-MORPHOLYL}ETHYLOXY)PHENYL-PENTYL]-O-[(2-PYRIDYL)METHYL]-D-VALINOL

The title compound is obtained from the phenol derivative of Example 18, Step C using the alkylation procedure described in Example 17, Step C.

STEP E
N-[4-N-BENZYLOXYCARBONYL-L-VALYL)AMINO-2,2-DIFLUORO-1,3-DIOXO-5-(4-{2-N-MORPHOLYL}ETHYLOXY)PHENYL-PENTYL]-O-[(2-PYRIDYL)METHYL]-D-VALINOL

The title derivative is obtained from the compound given in Example 18, Step D using the oxidation method described in Example 7, Step D.

The compounds of the present invention are useful as inhibitors of retroviral proteases required for replication, particularly the HIV-1 and HIV-2 viral proteases, the prevention or treatment of infection by the human immunodeficiency virus (HIV), and the treatment of consequent pathological conditions such as the acquired immunodeficiency syndrome (AIDS) in mammals capable of being infected with HIV virus. Treating AIDS, preventing infection by HIV or treating infection by HIV, is defined as including, but not limited to, treating a wide range of states of HIV infection: AIDS, ARC (AIDS related complex), both symptomatic and asymptomatic, and actual or potential exposure to HIV. For example, the compounds of this invention are useful in preventing infection by HIV after suspected past exposure to HIV by, e.g., blood transfusion, accidental needle stick, or exposure to patient blood during surgery.

The term "stereoisomers" is a general term for all isomers of individuals molecules that differ only in the orientation of their atoms in space. It includes mirror image isomers (enantiomers), geometric (cis/trans) isomers, and isomers of compounds with more than one chiral center that are not mirror images of one another (diastereoisomers). For amino-acids, the designations L/D, or R/S can be used as described in IUPAC-IUB Joint Commission on Biochemichal Nomenclature. Eur. J. Biochem. 138: 9–37 (1984).

For these purposes, the compounds of the present invention may be administered orally, parenterally (including subcutaneous injections, intravenous, intramuscular, transdermal, intrasternal injection or infusion techniques), by inhalation spray, or rectally, in dosage unit formulations containing convention non-toxic pharmaceutically acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays; steriel injectable preparations, for example, as sterile injectable aqueous or oleagenous suspensions or suppositories) or they may be administered transdermally.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweetener/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidize and/or dissolve in the rectal cavity to release the drug.

Dosage levels of the order of 0.02 to 5.0 or 10.0 grams per day are useful in the treatment or prevention of the above-indicated conditions, with oral doses being higher. For example, infection by HIV is effectively treated by the administration of from 1 to 50 milligrams of the compound per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination the severity of the particular condition, and the host undergoing therapy.

The present invention is also directed to combinations of the HIV protease-inhibitory compounds with one or more agents useful in the treatment of AIDS, such as, for example, with known antiviral agents suitable for treating HIV 1 and HIV 2 vital infections, e.g., AZT, with or without a PNPase inhibitor, or in conjunctive therapy with DDI and a PNPase inhibitor.

The compounds of this invention may be assayed for their HIV-protease inhibition using the following published techniques.

Preparation of Retroviral Enzyme and Assay for Inhibition of the Protease

A) Preparation of Retroviral Enzyme

To prepare the recombinant protease, the HIV protease was expressed via *E. Coli* by the published work of C. Guénet, et al., in European Journal of Pharmacology, Molecular Pharmacology Section, 172 (1989) 443–451.

B) Assay for Inhibition of Recombinant Vital Protease

Inhibition of the reaction of the protease with a peptide substrate [Ser-Gln-Asn-Tyr-Pro-Ile-Val-NH$_2$, Km=1 mM were in 50 mM Na acetate, 10% glycerol, 5% ethyleneglycol, pH 5.5, at 37° C. for 1 hour. Various concentrations of inhibitor in 10 µl DMSO were added to 80 µl of assay solution and the reaction initiated by the addition of 10 µl (1.6 µg) of recombinant protease. The reaction was quenched with 16 µl of 4M perchloric acid. Products of the reaction were separated by HPLC (VYDAC wide pore 5 cm C-18 reverse phase, acetonitrile gradient, 0.1% trifluoroacetic acid). The extent of inhibition of the reaction was determined from the peak heights of the products. HPLC of the products, independently synthesized, provided quantitation standards and confirmation of the product composition.

By following the techniques referenced above, as well as by utilization of other known techniques, as well as by comparison with compounds known to be useful for treatment of the above-mentioned disease states, it is believed that adequate material is available to enable one of ordinary skill in the art to practice the invention.

As is true for most classes of compounds found to be useful in the pharmaceutical industry, certain subgeneric groups and certain specific compounds are more preferred such as those exemplified and shown in the following chart. Within the concepts of this invention, it is to be found that the preferred compounds are those wherein R$_5$ is CH(Y)(Z) and P$_1$ is B, especially when T' is H.

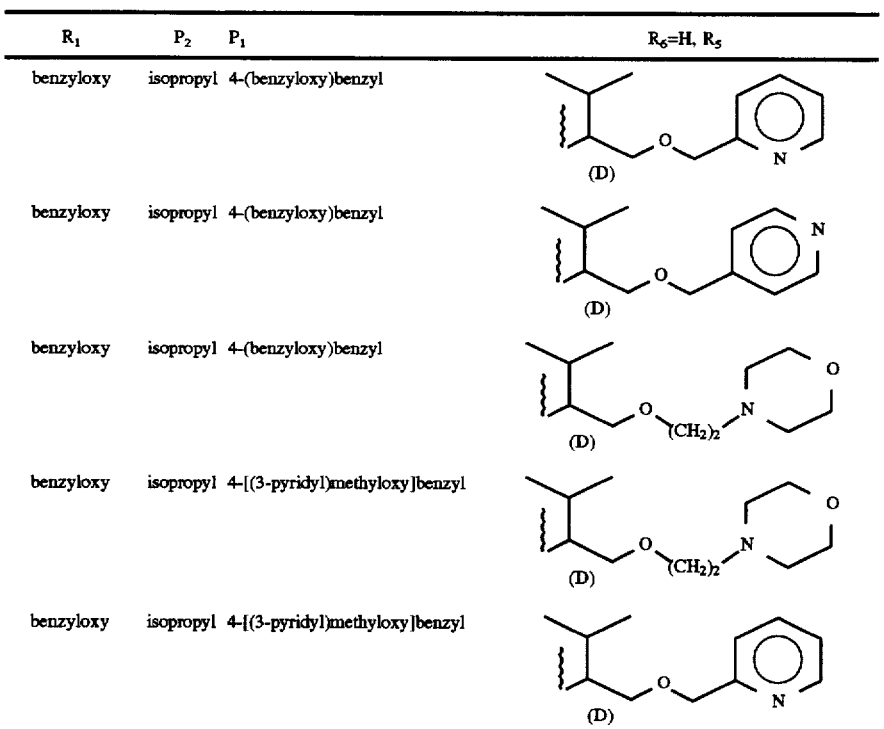

-continued

| R₁ | P₂ | P₁ | R₆=H, R₅ |
|---|---|---|---|
| benzyloxy | isopropyl | 4-[(2-pyridyl)methyloxy]benzyl | 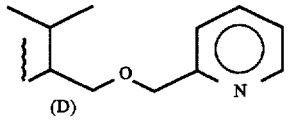 |
| benzyloxy | isopropyl | 4-[(2-pyridyl)methyloxy]benzyl | 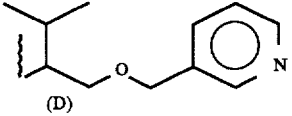 |
| benzyloxy | isopropyl | 4-[(3-pyridyl)methyloxy]benzyl | 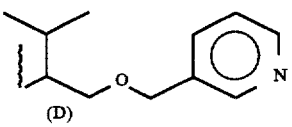 |
| (3-pyridyl)ethyl | isopropyl | 4-[(3-pyridyl)methyloxy]benzyl | 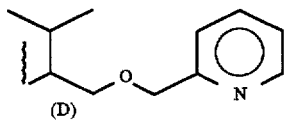 |
| (3-pyridyl)ethyl | isopropyl | 4-[(2-pyridyl)methyloxy]benzyl | 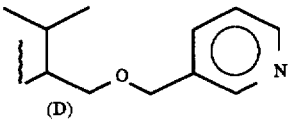 |
| benzyloxy | t-butyl | 4-[(2-pyridyl)methyloxy]benzyl | 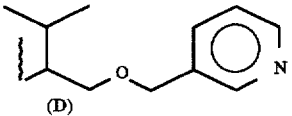 |
| benzyloxy | t-butyl | 4-[(3-pyridyl)methyloxy]benzyl | 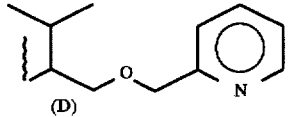 |
| benzyloxy | isopropyl | 4-(benzyloxy)benzyl | 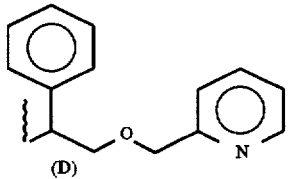 |
| benzyloxy | isopropyl | 4-[(3-pyridyl)methyloxy]benzyl | 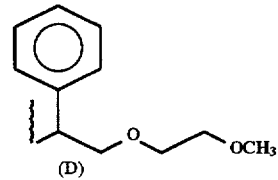 |
| benzyloxy | phenyl | 4-[(3-pyridyl)methyloxy]benzyl | 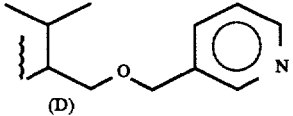 |
| benzyloxy | isopropyl | 4-[(2-pyridyl)methyloxy]benzyl | 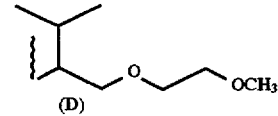 |

-continued

| R₁ | P₂ | P₁ | R₆=H, R₅ |
|---|---|---|---|
| benzyloxy | isopropyl | 4-[(2-pyridyl)methyloxy]benzyl | 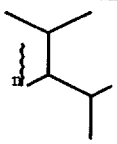 |
| (3-pyridyl)ethyl | isopropyl | 4-[(3-pyridyl)methyloxy]benzyl | 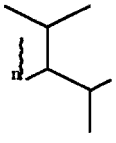 |
| (3-pyridyl)ethyl | isopropyl | 4-(benzyloxy)benzyl | 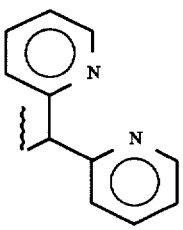 |
| benzyloxy | isopropyl | 4-[(3-pyridyl)methyloxy]benzyl | 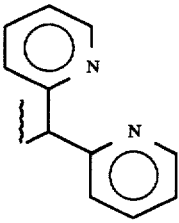 |
| benzyloxy | isopropyl | 4-[(3-pyridyl)methyloxy]benzyl | 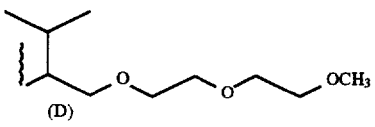 (D) |
| benzyloxy | isopropyl | 4-[(2-pyridyl)methyloxy]benzyl | 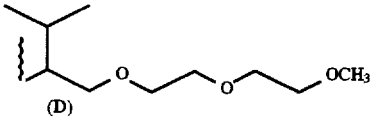 (D) |
| benzyloxy | isopropyl | 4-[2-(N-morpholyl)ethyloxy]benzyl | 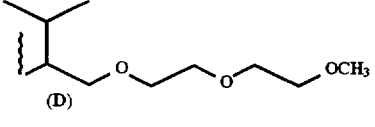 (D) |
| benzyloxy | t-butyl | 4-[2-(N-morpholyl)ethyloxy]benzyl | 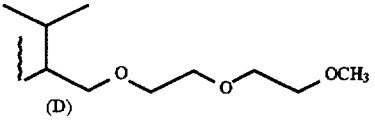 (D) |
| benzyloxy | isopropyl | 4-[2-(N-morpholyl)ethyloxy]benzyl | 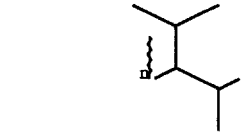 |
| benzyloxy | isopropyl | 4-[2-(N-morpholyl)ethyloxy]benzyl | 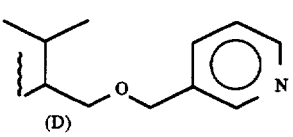 (D) |

| R₁ | P₂ | P₁ | R₆=H, R₅ |
|---|---|---|---|
| benzyloxy | t-butyl | 4-[2-(N-morpholyl)ethyloxy]benzyl | (D) |
| benzyloxy | t-butyl | 4-[2-(N-morpholyl)ethyloxy]benzyl | |
| benzyloxy | isopropyl | 4-[2-(N-piperidyl)ethyloxy]benzyl | (D) |
| benzyloxy | isopropyl | 4-[2-(N-piperidyl)ethoxyl]benzyl | (D) |
| benzyloxy | t-butyl | 4-[2-(N-piperidyl)ethyloxy]benzyl | (D) |
| benzyloxy | isopropyl | 4-[2-(N-piperidyl)ethyloxy]benzyl | (D) |

What is claimed is:

1. A compound which is N-[4-{N-Benzyloxycarbonyl-1-valyl)amino-2,2-difluoro-1,3-dioxo-5-(4-benzyloxy) phenyl-pentyl]-OO[(3-pyridyl)methyl]-D-valinol.

2. A compound which is 4-(N-Benzyloxycarbonyl-L-valyl)amino-2,2-difluoro-3-oxo-5-(4-benzyloxy)phenyl-N (1-isopropyl-2-methyl-propane)pentanamide.

3. A compound which is 4-[N-(3-Pyridylpropionyl)-L-valyl]amino-2,2-difluoro-3-oxo-5-( 4-benzyloxy)phenyl-N (1-isopropyl-2-methyl-propane)pentanamide.

4. A compound which is N-[4-(N-Benzyloxycarbonyl-L-valyl)amino-2,2-difluoro-1,3-dioxo-5-(4-benzyloxy) phenyl-pentyl]-di(O-benzyl)serinol.

5. A compound which is 4-(N-Benzyloxycarbonyl-L-valyl)amino-2,2-difluoro-3-oxo-5-(4-benzyloxy)phenyl-N (α-L-methyl)benzyl pentanamide.

6. A compound which is N-[4-(N-Benzyloxycarbonyl-L-valyl)amino-2,2-difluoro-1,3-dioxo-5-(4-benzyloxy) phenyl-pentyl]-O-(2-methoxyethoxymethyl]-D-valinol.

7. A compound which is N-[4-(N-Benzyloxycarbonyl-L-valyl)amino-2,2-difluoro-1,3-dioxo-5-(4-benzyloxy) phenyl-pentyl]-O-formyl-D-valinol.

8. A compound which is N-[4-(N-Benzyloxycarbonyl-L-valyl)amino-2,2-difluoro-1,3-dioxo-5-(4-benzyloxy) phenyl-pentyl]-O-[2-(2-methoxyethoxy)-1-ethyl]-D-valinol.

9. A compound which is 4-(N-Benzyloxycarbonyl-L-valyl)amino-2,2-difluoro-3-oxo-5-(4-benzyloxy)phenyl-N-benzydryl pentanamide.

10. A compound which is 4-(N-Benzyloxycarbonyl-L-valyl)amino-2,2-difluoro-3-oxo-5-(4-benzyloxy)phenyl-N [1,1-di(2-pyridyl)methyl]pentanamide.

11. A compound which is N-[4-(N-Benzyloxycarbonyl-L-valyl)amino-2,2-difluoro-1,3-dioxo-5-(4-{2-N-morpholyl}ethyloxy)phenyl-pentyl]-O-[(3-pyridyl)methyl]-D-valinol.

12. A compound which is N-[4-(N-Benzyloxycarbonyl-L-valyl)amino-2,2-difluoro-1,3-dioxo-(4-{2-N-morpholyl}ethyloxy)phenyl-pentyl]-O-[(2-pyridyl)methyl]-D-valinol.

* * * * *